US008540638B2

(12) United States Patent
Gourevitch

(10) Patent No.: US 8,540,638 B2
(45) Date of Patent: Sep. 24, 2013

(54) 3-D QUANTITATIVE-IMAGING ULTRASONIC METHOD FOR BONE INSPECTIONS AND DEVICE FOR ITS IMPLEMENTATION

(75) Inventor: Alla Gourevitch, Haifa (IL)

(73) Assignee: Alla Gourevitch, Haifa (IL)

( * ) Notice: Subject to any disclaimer, the term of this patent is extended or adjusted under 35 U.S.C. 154(b) by 417 days.

(21) Appl. No.: 13/007,795

(22) Filed: Jan. 17, 2011

(65) Prior Publication Data

US 2011/0112404 A1 May 12, 2011

Related U.S. Application Data

(63) Continuation-in-part of application No. 12/444,599, filed on Apr. 7, 2009, now abandoned, which is a continuation-in-part of application No. PCT/IL2007/001283, filed on Oct. 24, 2007.

(60) Provisional application No. 60/853,759, filed on Oct. 24, 2006.

(51) Int. Cl.
*A61B 8/00* (2006.01)

(52) U.S. Cl.
USPC ............ 600/447; 600/449; 600/407; 600/437

(58) Field of Classification Search
None
See application file for complete search history.

(56) References Cited

U.S. PATENT DOCUMENTS

| | | | |
|---|---|---|---|
| 4,421,119 A | 12/1983 | Pratt, Jr. | |
| 4,926,870 A | 5/1990 | Brandenburger | |
| 5,143,072 A | 9/1992 | Kantorovich | |
| 6,012,799 A | 1/2000 | Silverbrook | |
| 6,221,019 B1 | 4/2001 | Kantorovich | |
| 6,305,060 B1 | 10/2001 | Morris | |
| 6,371,916 B1 | 4/2002 | Buhler | |
| 6,432,057 B1 | 8/2002 | Mazess | |
| 6,517,487 B1 | 2/2003 | Mazess | |
| 2002/0099290 A1 | 7/2002 | Haddad | |
| 2002/0134178 A1 | 9/2002 | Knight | |
| 2003/0018263 A1 | 1/2003 | Morris | |
| 2003/0055334 A1 | 3/2003 | Steinbacher | |
| 2003/0055337 A1 | 3/2003 | Lin | |
| 2004/0193047 A1 | 9/2004 | Pelissier | |
| 2005/0004979 A1 | 1/2005 | Berkowitz | |

(Continued)

OTHER PUBLICATIONS

C.M. Langton, S.B. Palmer, R. W. Porter, The Measurement of Broadband UltrasonicAttenuation in Cancellous Bone, Engineering in Medicine MEP Ltd. 1984, vol. 13, No. 2, pp. 89-91.

(Continued)

*Primary Examiner* — Unsu Jung
*Assistant Examiner* — Saurel J Selkin
(74) *Attorney, Agent, or Firm* — Marsteller & Associates, P.C.

(57) ABSTRACT

The invention is a differential 3D Quantitative-Imaging Ultrasonic Tomography method for inspecting a layered system that is comprised of a heterogeneous object embedded in a volume of space that comprises layers having an acoustic impedance gradient between the layers providing non-linear beams travels. A transducer grid is attached to the surface of the layered system in a unilateral manner. By sequentially changing the distance between transmitter and receiver the fastest travel times of the ultrasonic oscillations are measured. A differential approach provides from the data the longitudinal wave velocities values for each elementary volume that make up an inspected volume. These values are used to construct two and three-dimensional maps of the longitudinal wave velocity values distribution in the inspected volume and the porosity values distribution in the heterogeneous object. By applying statistical treatment to the obtained data the longitudinal wave velocity in the inspected material matrix part is estimated.

19 Claims, 20 Drawing Sheets

(56) References Cited

U.S. PATENT DOCUMENTS

2005/0033140 A1 2/2005 de la Rosa
2005/0107700 A1 5/2005 Morris
2005/0117694 A1 6/2005 Francke
2005/0124886 A1 6/2005 O'Donnell

OTHER PUBLICATIONS

M.R.J. Wyllie, A.R. Gregory, and G.H.F. Gardner, Art Experiemental Investigation of Factors Affecting Elastic Wave Velocities in Porous Media, Geophysics, vol. XXIII, No. 3, Jul. 1958, pp. 459-493.

Elinor R. Hughes, Timothy G. Leighton, Graham W. Petley, Paul R. White, Ultrasonic Assessment of Bone Health, Acoustics Bulletin, Sep./Oct. 2001, pp. 17, 19-23.

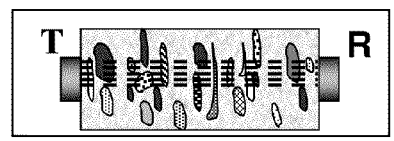 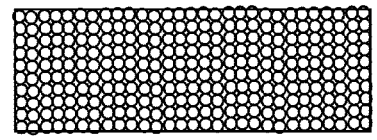
Fig. 2A        Fig. 2B
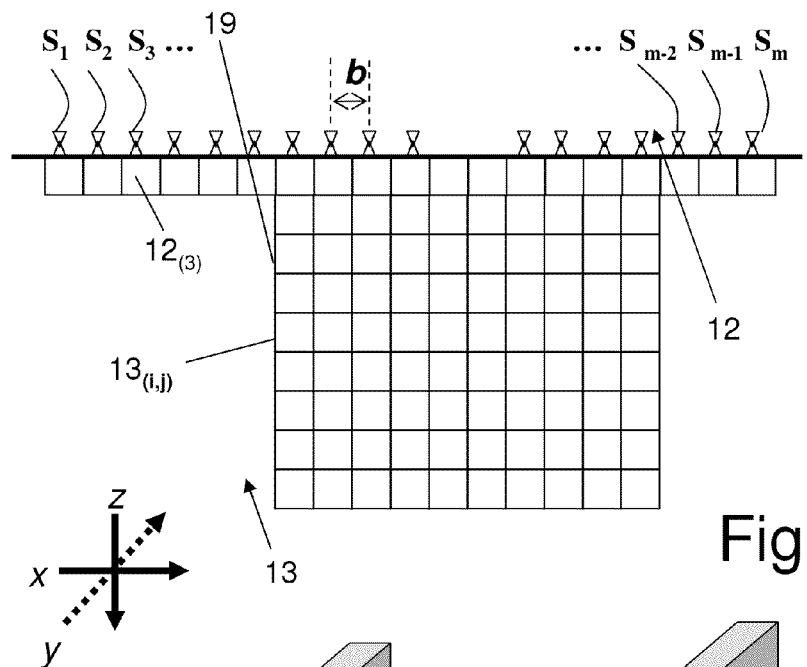
Fig. 2C
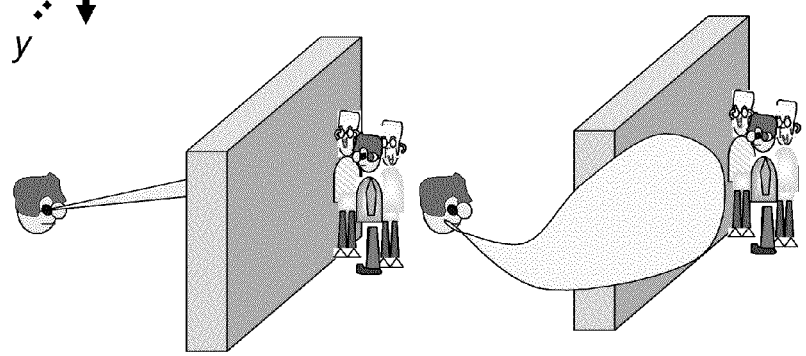
Fig. 2D        Fig. 2E □ 200-500   □ 500-800   ■ 800-1100   ■ 1100-1400
■ 1400-1700 ■ 1700-2000 □ 2000-2300  ■ 2300-2600
■ 2600-2900 ■ 2900-3200 ■ 3200-3500  m/s Table 1

| Route | Distance | Measurement time in the route (-m) to (m), $\tau_m$ µs | | Measurement time in the route (-m+1) to (m-1), $\tau_{m-1}$, µs | | Measurement time in the route (-m+1) to (m), $\tau_{dir}$, µs | | Measurement time in the route (-m) to (m-1), $\tau_{rec}$, µs | |
|---|---|---|---|---|---|---|---|---|---|
| | cm | Direct, $\tau_{m,dir}$ | Reciprocal, $\tau_{-m+1,dir}$ | Direct, $\tau_{-m+1,dir}$ | Reciprocal, $\tau_{-m+1,rec}$ | Direct, $\tau_{dir,dir}$ | Reciprocal, $\tau_{dir,rec}$ | Direct, $\tau_{rec,dir}$ | Reciprocal, $\tau_{rec,rec}$ |
| 1 | 2 | 3 | 4 | 5 | 6 | 7 | 8 | 9 | 10 |
| Section 10.8cm | | | | | | | | | |
| 5to32 | 10,8 | 172 | 172 | 162 | 160 | 168 | 167 | 169 | 169 |
| 6to31 | 10 | 162 | 160 | 151 | 153 | 157 | 157 | 157 | 156 |
| 7to30 | 9,2 | 151 | 153 | 142 | 140 | 146 | 143 | 147 | 147 |
| 8to29 | 8,4 | 142 | 140 | 129 | 132 | 137 | 137 | 136 | 136 |
| 9to28 | 7,6 | 129 | 132 | 111 | 122 | 113 | 126 | 118 | 121 |
| 10to27 | 6,8 | 111 | 122 | 100 | 107 | 103 | 109 | 100 | 107 |
| 11to26 | 6 | 100 | 107 | 92 | 93 | 96 | 99 | 98 | 96 |
| 12to25 | 5,2 | 92 | 93 | 89 | 88 | 89 | 88 | 88 | 89 |
| Section 10cm | | | | | | | | | |
| 5to30 | 10 | 161 | 163 | 152 | 152 | 157 | 156 | 157 | 158 |
| 6to29 | 9,2 | 152 | 152 | 140 | 143 | 147 | 147 | 147 | 148 |
| 7to28 | 8,4 | 140 | 143 | 130 | 132 | 136 | 136 | 137 | 136 |
| 8to27 | 7,6 | 130 | 132 | 111 | 118 | 118 | 121 | 121 | 127 |
| 9to26 | 6,8 | 111 | 118 | 102 | 102 | 100 | 107 | 106 | 112 |
| 10to25 | 6 | 102 | 102 | 92 | 91 | 98 | 96 | 103 | 96 |
| 11to24 | 5,2 | 92 | 91 | 88 | 86 | 88 | 89 | 86 | 86 |
| Section 9.2cm | | | | | | | | | |
| 5to28 | 9,2 | 151 | 151 | 141 | 141 | 147 | 148 | 147 | 138 |
| 6to27 | 8,4 | 141 | 141 | 131 | 131 | 137 | 136 | 136 | 136 |
| 7to26 | 7,6 | 131 | 131 | 112 | 120 | 121 | 127 | 122 | 126 |
| 8to25 | 6,8 | 112 | 120 | 106 | 108 | 106 | 112 | 112 | 111 |
| 9to24 | 6 | 106 | 108 | 92 | 90 | 103 | 96 | 100 | 102 |
| 10to23 | 5,2 | 92 | 90 | 88 | 87 | 86 | 86 | 86 | 86 |

Fig. 18

Table 2

| Distance, cm | Δt, μs according to the algorithm | | | $t_m$, μs (15,29+Δt) | | | Longitudinal wave velocity, V, m/s s/$t_m$ | | |
|---|---|---|---|---|---|---|---|---|---|
| | Section, cm | | | | | | | | |
| | 10,8 | 10 | 9,2 | 10,8 | 10 | 9,2 | 10,8 | 10 | 9,2 |
| 10,8 | -3,5 | 0 | 2 | 11,8 | 15,3 | 17,3 | 2129 | 1642 | 1452 |
| 10 | -0,5 | -1 | -0,5 | 14,8 | 14,3 | 14,8 | 1697 | 1757 | 1697 |
| 9,2 | 1,5 | 0 | -1 | 16,8 | 15,3 | 14,3 | 1495 | 1641 | 1757 |
| 8,4 | -1,5 | 2 | 2,5 | 13,8 | 17,3 | 17,8 | 1820 | 1452 | 1411 |
| 7,6 | 8 | 4 | -2,5 | 23,3 | 19,3 | 12,8 | 1078 | 1301 | 1963 |
| 6,8 | 10,5 | -3 | 6,5 | 25,8 | 12,3 | 21,8 | 973 | 2042 | 1152 |
| 6 | 1,5 | 4 | | 16,8 | 19,3 | | 1495 | 1302 | |
| 5,2 | 4 | | | 19,3 | | | 1301 | | |

Fig. 19

Table 3

| | The longitudinal wave velocity values, m/s | | | | |
|---|---|---|---|---|---|
| Distance, cm | Distance, cm | | | | |
| | 4,5 | 5,3 | 6,1 | 6,9 | 7,7 |
| 10,4 | 3213 | 2834 | 3443 | 2534 | 4388 |
| 11,2 | 3213 | 3709 | 2407 | 3213 | 2407 |
| 12 | 3443 | 3709 | 3443 | 3709 | 3011 |
| 12,8 | 3709 | 2834 | 2092 | 28334 | 2834 |
| 13,6 | 3709 | 2834 | 2534 | 4020 | 4388 |
| 14,4 | 2834 | 3213 | 4510 | 4490 | 3443 |
| 15,2 | 1718 | 1603 | 2092 | 4490 | 2005 |
| 16 | 2534 | 3011 | 3709 | 2407 | 3213 |
| 16,8 | 2407 | 2834 | 3443 | 3213 | 4388 |
| 17,6 | 3011 | 3443 | 4020 | 2834 | 1659 |
| 18,4 | 4388 | 2676 | 2534 | 2834 | 3213 |
| 19,2 | 2534 | 4020 | 3011 | 2834 | 4020 |

Fig. 20

Table 4

| The porosity values | | | | | |
|---|---|---|---|---|---|
| Distance, cm | 4,5 | 5,3 | 6,1 | 6,9 | 7,7 |
| 10,4 | 0,260 | 0,352 | 0,213 | 0,444 | 0,075 |
| 11,2 | 0,260 | 0,167 | 0,491 | 0,260 | 0,491 |
| 12 | 0,213 | 0,167 | 0,213 | 0,167 | 0,306 |
| 12,8 | 0,167 | 0,352 | 0,629 | 0,352 | 0,352 |
| 13,6 | 0,167 | 0,352 | 0,444 | 0,121 | 0,075 |
| 14,4 | 0,352 | 0,260 | 0,061 | 0,063 | 0,213 |
| 15,2 | 0,860 | 0,952 | 0,629 | 0,063 | 0,675 |
| 16 | 0,444 | 0,306 | 0,167 | 0,491 | 0,260 |
| 16,8 | 0,491 | 0,352 | 0,213 | 0,260 | 0,075 |
| 17,6 | 0,306 | 0,213 | 0,121 | 0,352 | 0,906 |
| 18,4 | 0,075 | 0,398 | 0,444 | 0,352 | 0,260 |
| 19,2 | 0,444 | 0,121 | 0,306 | 0,352 | 0,121 |

Fig. 21

3-D QUANTITATIVE-IMAGING ULTRASONIC METHOD FOR BONE INSPECTIONS AND DEVICE FOR ITS IMPLEMENTATION

This is a continuation-in-part of U.S. Ser. No. 12/444,599, filed Apr. 7, 2009, now abandoned, which is a continuation-in-part of PCT/IL2007/001283 (WO 2008/050333) filed Oct. 24, 2007, which claims priority to 60/853,759, filed Oct. 24, 2006, the contents of which are incorporated herewith.

FIELD OF THE INVENTION

The present invention relates to the field of quantitative-imaging ultrasound technology and equipment. In particular, the invention relates to the field of as ultrasonic imaging in medical diagnostics and non-medical applications.

BACKGROUND OF THE INVENTION

A significant number of ultrasonic methods, which provide for imaging of soft tissues of a human body, exist. They are based for example on the Compound Imaging approach, Stereoscopic imaging, Harmonic imaging, the Spatial Compounding Approach, and other methods. These methods are disclosed for example in: U.S. Pat. No. 6,517,487 and in U.S. Patent Applications 2003/0055334, 2003/0055337, 2004/0193047, 2005/0033140, 2005/0049479, 2005/0124886, 2005/0117694, and other patents and applications.

Because of the high attenuation coefficient of a bone compared with a soft tissue, ultrasonic imaging methods known in the art are unsuitable for assessing the skeleton of a human body. Therefore, the conventional ultrasonic imaging systems that are used for studying soft tissue are also not optimized for assessing the skeleton.

Ultrasonic methods for simultaneously quantitative and imaging measurements are known in the art. For example, United States Patent Application 2003/0018263; to Morris, et al; entitled Multi-Zone Transmitter For Quantitative Ultrasound And Image Measurement; filed: Jul. 20, 2001; discloses an ultrasonic transmission unit for an imaging/quantitative ultrasound device provides for coaxial transducer crystals which may be operated independently with a first crystal operated alone for quantitative measurement and the first and second crystal operated together to provide a broad illumination for imaging of structure.

U.S. Patent Application 2005/0107700 proposes a thin film piezoelectric material employing a metallic backer plate to provide high output, non-resonant ultrasonic transmissions suitable for quantitative ultrasonic measurement and/or imaging. Thin film polymer piezoelectric materials such as polyvinylidene fluoride (PDVF) may also be used as an ultrasonic transducer as described in the U.S. Pat. No. 6,305,060 and U.S. Pat. No. 6,012,779.

Ultrasonic investigations of the skeleton can be carried out using the Quantitative UltraSonography (QUS) method. The main ultrasonic parameters evaluated in QUS measurement are the Speed of Sound (SOS) and the frequency dependence of attenuation.

Ultrasonic Attenuation (BUM technique is described by Langton C M, Palmer S B, Porter R W, The Measurement of Broadband Ultrasonic Attenuation in Trabecular Bone, Engineering in Medicine, 13 3, 89-91 (1984). Whilst it now forms the basis of clinical QUS bone assessment, this empirical method is not entirely satisfactory, The BUA technique essentially measures insertion loss, found by comparing the amplitude spectrum of an ultrasonic pulse through bone with the amplitude spectrum of an ultrasonic pulse through a reference medium, typically water. The assumption is made that the attenuation, a (f), is a linear function of frequency, f, between 200-600 kHz. However, a number of authors argued that the assumption of linear relationship does not have any physical basis. (Elinor R Hughes MIOA, Timithy G Leighton FIOA, Graham W Petley, Paul R White "Ultrasonic assessment of bone health" (www.isrt.soton.ac.uk)

U.S. Pat. No. 6,371,916; entitled Acoustic Analysis of Bone Using Point-Source-Like Transducers; to Buhler, et al.; filed: Sep. 3, 1999; discloses an improved apparatus and method for providing a measurement of the characteristic behavior of an acoustic wave in a bone of a subject. A preferred embodiment has first and second transducers and a mounting arrangement for mounting the transducers in spaced relationship with respect to the bone. The first transducer may transmit acoustic energy over a broad solid angle, thereby behaving as a point source of acoustic energy. Additionally or alternatively, the second transducer may collect acoustic energy over a broad solid angle, thereby behaving as a point receiver. A signal processor in communication with the second transducer provides a measurement that is a function of at least one of transient spectral or transient temporal components of the signal received by the second transducer.

U.S. Pat. No. 6,371,916 describes the first invention that proposes an approach for estimation of bone porosity. The invention disclosed in this patent provides a method of determining an index of porosity, which is an indirect qualitative but not quantitative parameter that gives an estimation of porosity and non-connectivity of a bone. However the method does not allow estimates of the value of porosity, images of the distribution of porosity values in a considered volume, or 3D imaging of bones in a human body. It does not provide.

A method for determining porosity value for the inspected media is known from the field of oil geophysics. This method uses a modified Wyllie relationship which can be found in Wyllie, M. R., An experimental investigation of factors affecting elastic wave velocities in porous media, Geophysics, vol. 23, No. 3, 1958. But this approach does not provide values for the porosity distribution in a volume being inspected.

An acoustic energy may travel, reflect, and refract on a boundary between media with different acoustic impedances. Traveling acoustic energy is used in the direct transmission method. For example the U.S. Pat. Nos. 4,926,870; 4,421,119 are described systems, which place a receiver and a transmitter on opposite sides of a bone. The linear propagation of elastic waves is used in the method. This is the conventional method used for bone tissue inspections. The method provides integral estimations. The obtained data is characterized by integral estimations about the travel time from a transmitter to a receiver of longitudinal waves in heterogeneous objects, specifically bones. In the case investigations of heterogeneous object parameters of the object being investigated may increase in one part of an investigated object and decrease in another-part. Significant mistakes in the values of the parameters are therefore obtained because the method is not sensitive to changes in structure of the object and it ignores a heterogeneous property of the object and its anisotropy.

Inspection methods based on refracted energy are used in industry. For example, Time of Flight Diffraction technique (TOFD) is disclosed in U.S. Patent Application 20020134178; to Knight, et al.; entitled Ultrasonic Testing System. In this method a probe with different beam angles is used to detect planar defects by varying an angle of orientation. Usually two probes, one transmitter and one receiver, are arranged on an object's surface. The transmitter sends a relatively wide beam for maximizing the field of the scan. Both probes are aligned geometrically on the same side of an object being studied and A-scans are taken at sequential positions along the length of the object. The data collection on site by the TOFD method is faster than most conventional methods because it uses wide ultrasonic beams for imaging. It is a technique for precise depth assessment. However, this technique does not apply for investigations of anisotropic and heterogeneous materials and is not used in medicine.

Contrary to X-ray CT, Ultrasonic tomography of elastic wave velocities has not found general practical usage in medical imaging. The main problems are deviation of the ultrasound beam due to reflection and refraction caused by gas and bone inclusions in the heterogeneous media.

The use of elastic wave refraction for investigations of bone structure in a human body for medical diagnostics is described in the U.S. Pat. No. 6,221,019 and U.S. Pat. No. 5,143,072. The disclosed methods assume that the refracted waves travel in the field with a boundary between layers with different acoustic impedance, i.e. the boundary between tissue and bone. In the disclosed patents, a transmitter and a receiver are placed on the skin of a patient facing a bone. Ultrasonic waves are transmitted along a transmission path from the transmitter to the bone through the soft tissue surrounding the bone, along the surface of the bone and back through the soft tissue to the receiver at location 1 and location 2. The travel times of the fastest signals between the transmitter and receiver (for location 1 and for location 2) are measured and the acoustic velocity of the bone is calculated based on the distance between the transmitter and the receiver's two locations, the thickness of the soft tissue and the acoustic velocity in the soft tissue. The reflected waves are used for estimations of the acoustic velocity and thickness of soft tissues. The measured parameter, Speed of Sound (SOS) of a cortical bone is calculated from the obtained measured data.

However, this method has the several serious shortcomings. The method is based only on two layers of soft tissue and bone. The method cannot account for anisotropy and the heterogeneous nature of the media of which the bone is comprised and thus produces an integral estimation that does not account for the influence of different parts of an inspected heterogeneous media and therefore leads to significant errors. The method does not map the distribution of changes in a bone by means of an estimated spatial distribution of parameters of the bone's medium. The method does not provide 3D imaging of the volume of the inspected bone. The method suffers an additional inaccuracy and inconvenience caused by the necessity of measuring thickness and longitudinal wave velocity in soft tissues by applying an additional Pulse-Echo method. The method does not estimate the mineral part (matrix) of an inspected bone, porosity values, and porosity distributions in a bone's volume. The method does not provide the locations and estimations of the risk of fracture. The method utilizes high frequency ultrasonic oscillations.

SUMMARY OF THE INVENTION

In a first aspect the invention is a differential method of 3D Quantitative-Imaging Ultrasonic Tomography for inspecting a layered system comprised of a heterogeneous object embedded in a volume of space that comprises layers having an acoustic impedance gradient between the layers. The acoustic impedance gradient causes non-linear elastic wave propagation of ultrasonic oscillations through the volume of space. The method comprises the steps of:

a) Providing two or more transducers arranged in a line or as a two-dimensional array on one side of the layered system and in acoustic contact with the upper layer of the layered system. The transducers are capable being activated to either transmit or to receive the ultrasonic oscillations.
b) Sequentially activating one of the transducers as a transmitter and others of the transducers as receivers of the ultrasonic oscillations to measure the fastest travel times for sequential transmitter/receiver pairs with sequentially changing distances between transmitter and receiver.
c) Virtually dividing the volume of space into elementary volumes.
d) Using a differential approach to determine values of the longitudinal wave velocity for each of the elementary volume. and
e) Applying an ultrasonic computer tomography approach to construct two-dimensional and three-dimensional maps of the distributions of the longitudinal wave velocity values in the volume of space.

An embodiment of the method of the invention comprises the steps of:

a) Determining the correct magnitude of low frequency ultrasonic oscillations to be used with the transducers and the arrangement of the transducers for the inspection in a specific application.
b) Activating a first transducer to transmit ultrasonic oscillations in the direction of an object being observed and activating the remaining transducers to receive elastic waves that have traveled through the observed system.
c) Measuring the fastest time of travel between each transmitter-receiver pair and storing the travel times for later use.
d) Repeating the measurements sequentially by changing the distance between transmitter and receivers by a fixed distance equal to distance between transducers each time.
e) Repeating measurements of steps b), c), and d) in the reciprocal direction.
f) Moving the line of transducers parallel to the original line or activating a second line of transducers in a two dimensional grid of transducers and repeating the measurements of steps b), c), d), and e) in the direct and reciprocal directions until data is obtained from each line in the transducer grid.
g) Dividing virtually the volume of space containing the layered system into elementary volumes situated in columns and rows; thereby enabling use of a differential approach to processing the obtained data.
h) Determining from the obtained data the values of the changes in the longitudinal wave travel time in each of the elementary volumes relative to the elementary volume located above it in the column from average values of the longitudinal wave travel times for neighboring routes in direct and reciprocal directions. The determination comprises the steps of:
i) Choosing two pairs of transducers located at two neighboring points equidistant from the axis of a column of elementary volumes.
ii) Summing the values of the travel time for ultrasonic oscillations between the transducers of each of the pairs that are furthest from the axis and the travel time for ultrasonic oscillations between the transducers of each of the pairs that are closest to the axis.
iii) Subtracting from the sum obtained in step ii the travel times for ultrasonic oscillations between the transducer of the pair of transducers located on a first side of said axis that is closest to said axis and the transducer of said pair of transducers that is located on the second side of said axis that is furthest from said axis.

iv) Subtracting from the sum obtained in step iii the travel times for ultrasonic oscillations between the transducer of the pair of transducers located on a first side of said axis that is furthest from said axis and the transducer of said pair of transducers that is located on the second side of said axis that is closest to said axis.

v) Repeating steps i to iv using different pairs of transducers for each of the elementary volumes in the column. and vi) repeating steps i to v for each column of elementary volumes in the volume of space containing the layered system.

i) Determining the values of longitudinal wave travel times for each elementary volume in each virtual vertical column of elementary volumes by using the known or previously measured value of the longitudinal wave travel time in the first elementary volume from the surface and by successively adding the values of the changes of the longitudinal wave travel times for the elementary volumes below the first one in the column;

j) Estimating the lengths of travel of the longitudinal wave through each of the elementary volumes;

k) Determining the longitudinal wave velocity values in each of the elementary volumes by dividing the estimated lengths of travel of the longitudinal wave through each of the elementary volumes by the values of longitudinal wave travel times for each elementary volume in each virtual vertical column of elementary;

l) Building pixel-by-pixel images of two dimensional horizontal or vertical sections from the longitudinal wave velocity values in each of the elementary volumes. and m) Combining the two dimensional images along a third axis with a constant step to build three dimensional images showing the longitudinal wave velocity values in the volume of space.

In embodiments of the method of the invention at least some of the steps can be carried out in a different order.

In embodiments of the invention the correct magnitude of low frequency ultrasonic oscillations to be used with the transducers and the arrangement of the transducers for the inspection in a specific application are determined using the following criteria:

a) The frequency is chosen such that the length of the applied oscillations is comparable to the dimensions of the inspected heterogeneous object. and b) The distance between the first transmitting transducer and the last receiving transducer in the line must be much greater than the dimensions of the inspected heterogeneous object.

In embodiments of the invention the ultrasonic oscillations are transmitted in the direction of an object being observed at an angle of no more than ninety degrees.

In embodiments of the invention the minimum distance between a transmitting transducer and a receiving transducer is two to three wavelengths of the applied oscillations.

In embodiments of the invention the length of travel of the longitudinal wave in each elementary volume is approximated by assuming that the longitudinal waves travel the same distance in each of the elementary volumes beneath the elementary volumes of the first layer of layered system. This distance is half the circumference of a circle having radius b, where b is the distance between adjoining transducers. It is also assumed that the wave travels in straight lines through the elementary volumes of the first layer, therefore the length of travel time in the first layer is $2b/\sin \alpha$ where $\alpha$ is the incident angle of the oscillations on the first layer.

In embodiments of the invention the acoustic properties of the uppermost elementary volumes are known or can be calculated in one of the following ways:

a) by implementing the first layer of the system as an additional plate or pillow having known acoustic properties; and b) by immersing the system in a container with liquid having known acoustic properties.

In embodiments of the invention a combination of signals from eight beams transmitted in the direct and reciprocal directions is employed to determine the properties of a specific elementary volume in the observed object. In other embodiments of the invention a combination of signals from four beams transmitted in the direct direction or four beams transmitted in the reciprocal direction is employed to determine the properties of a specific elementary volume in the observed object.

Embodiments of the invention further comprise the steps of:

a) Applying statistical treatment to the longitudinal wave velocity values obtained in step l) to determine the maximum value of the longitudinal wave velocity;

b) Identifying the matrix (skeleton) mineral part of an observed object, wherein the material matrix part of the object corresponds to elementary volumes that have the maximum value of longitudinal wave velocity;

c) Determining the values of porosity for each elementary volume of an observed volume by use of the modified Wyllie relationship for objects wherein the porous space is filled with liquid;

d) Building pixel-by-pixel images of two dimensional horizontal or vertical sections from the values of porosity for each elementary volume; and e) Combining the two dimensional images along a third axis with a constant step to build three dimensional images showing the porosity values in the observed volume.

In embodiments of the invention the layered system is a human or animal body wherein the layers comprise skin, fat, periosteum, cartilage, and muscle and bones are considered as localized heterogeneous bodies embedded in the layered system.

In embodiments of the invention the obtained maps are analyzed by observing decreases in the values of the elastic wave velocities and increases in porosity values that are shown in different areas of the images reveals defective areas in the inspected object. If the obtained images are of parts of a human or animal body that include bone material, the defective areas can be problematical zones with fracture risk. Estimates of the magnitude of the risk of fracture and revealing the location of the risk can be realized from the images by calculating the ratio of relative changes of the longitudinal wave velocity values for the defective area divided by the longitudinal wave velocity in the material matrix of the object.

In embodiments of the invention analysis of the obtained maps is carried out to provide information about internal organs of an individual and to reveal changes in the properties of the organs.

In embodiments of the invention at least one of the layers of the layered system is an artificial layer that is applied to create a layered system having a gradient of acoustic impedance that allows the differential method to be carried out.

In embodiments of the invention the elementary volumes are cubes having sides equal in length to the distance between two adjacent lines on the 2D planar grid or distance between transducers.

In embodiments of the invention inspecting a layered system comprises inspecting homogeneous material accommodated in the layered system, which is characterized by an acoustic impedance gradient.

In another aspect the invention is an Ultrasonic Tomograph apparatus adapted to carry out the method of the first aspect of the invention. The apparatus comprises:

a) a signal generator adapted to produce electronic signals in the form of short pulses of ultrasonic oscillations;
b) two or more transducers capable of transmitting and receiving ultrasonic oscillations arranged in a line or as a two-dimensional array;
c) a scanner position controller adapted to:
   i) direct the generated signals to the transducers; and
   ii) control the orientation of the transducers;
d) a time measuring unit adapted to receive signals from transducers acting as receivers and to amplify, filter, and process the signals to measure the shortest travel times along the direct and reciprocal paths. between transmitter/receiver pairs of the transducers;
e) a signal processor adapted to receive the measured travel times in digital format and to use the computational method of the invention to determine the differential data;
f) a storage device adapted to store the data;
g) an image formation unit adapted to:
   i) use the obtained differential data associated with a plurality of elementary volumes for pixel-by-pixel image mapping of the distribution of properties of the object that is being inspected; and
   ii) to analyze the maps that have been obtained; and
h) a display unit adapted to display the results of the mapping and/or analysis.

In embodiments of the invention the functions of the signal processor, the storage device, the image formation unit, and the display unit are combined in a single device.

In embodiments of the invention the transducers acting as transmitters are oriented at an angle that "points towards" the transducers acting as receivers. In order to change the mode of a transducer from that of a transmitter to that receiver it is necessary to change its orientation.

In embodiments of the invention the area of the transducer array may be smaller than the surface area of the region to be investigated. In these embodiments the transducer array can be moved to different locations on the surface of the layered system.

In embodiments of the invention comprising transducers arranged as a two-dimensional array the transducers of two or more lines of the array may be activated simultaneously to transmit and receive signals in the direct and the reciprocal directions.

All the above and other characteristics and advantages of the invention will be further understood through the following illustrative and non-limitative description of embodiments thereof, with reference to the appended drawings. In the drawings the same numerals are sometimes used to indicate the same elements in different drawings.

BRIEF DESCRIPTION OF THE DRAWINGS

FIG. 2A schematically demonstrates the prior art integral approach to quantitative ultrasonic imaging;

FIG. 2B schematically demonstrates the differential approach to quantitative ultrasonic imaging of the present invention;

FIG. 2C schematically depicts the division of one vertical slice columns and rows and shows the locations of the transducers;

FIG. 2D schematically shows the way in which high frequency ultrasonic oscillations elastic waves propagate and the effect obtained;

FIG. 2E schematically shows the way in which low frequency ultrasonic oscillations elastic waves propagate and the effect obtained;

FIG. 18 shows Table 1, which depicts data obtained in an experiment and its treatment according to the method of the current invention;

FIG. 19 shows Table 2, which depicts the sequence of the calculations and calculated values derived from the measured data for an experiment carried out on a specimen comprised of predominantly soft tissue;

FIG. 21 shows Table 3, which depicts the calculated longitudinal wave velocity values for an experiment carried out using a specimen characterized by predominantly bone tissue; and FIG. 21 shows Table 4, which depicts calculated porosity values for a specimen characterized predominantly by bone tissue.

DETAILED DESCRIPTION OF EMBODIMENTS OF THE INVENTION

Figure 1:
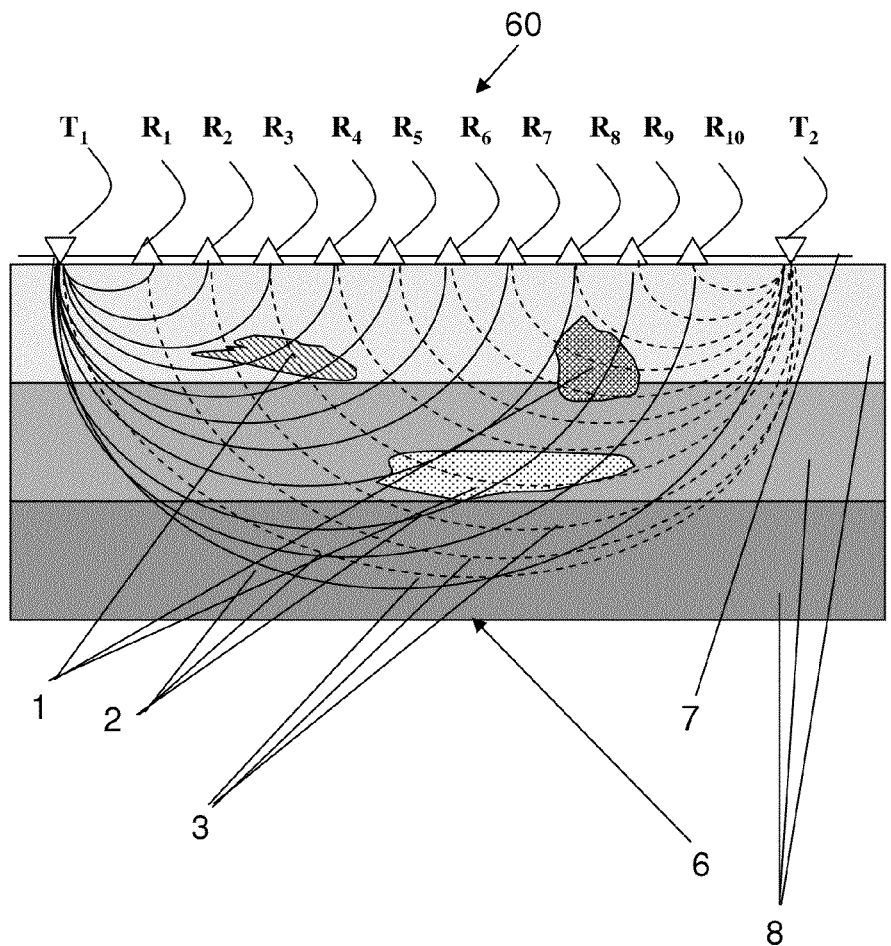
FIG. 1 schematically depicts the principle of the prior art Geophysical Tomographical method for a layered system.

Before describing at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

The drawings are generally not to scale. For clarity, non-essential elements were omitted from some of the drawings.

As used herein, an element or step recited in the singular and proceeded with the word "a" or "an" should be understood as not excluding plural elements or steps, unless such exclusion is explicitly recited.

The invention proposes a novel approach to data measurements and treatments providing the possibility for inspecting real heterogeneous and anisotropic substances by way of providing information about longitudinal wave velocity and porosity values for each elementary volume from which the inspected object is composed.

The strength of a bone is determined by two parameters: the amount and distribution of the bone mineral part and the volume and locations of the pores. The present invention allows these two parameters to be determined simultaneously and independently of each other, thereby allowing detailed 3D imaging and estimates of the quality of the bone. This is as opposed to the prior art integral methods that can only give parameters such as Bone Mineral Density (BMD) which represent the average influence of the mineral part and the pores to the strength of a bone.

Herein the following definitions are used:

The "integral" approach used in the prior art for measurement and treatment of data gathered related to a medium through which some form of energy is transmitted, e.g. ultrasound or x-rays, measures the average parameters of the medium through which the energy passes. For example, when ultrasound energy is passed through a non-homogeneous medium, the detector records the sum of the parameter being measured by all parts of the medium and no specific information can be gained concerning the influence of the different components that are present.

The "differential" approach of the present invention, as will be described in detail herein, provides information about the parameters of the medium estimated for each elementary volume and makes possible the application of Ultrasonic Computer Tomography. The invention also proposes a method of adapting for the first time approaches employed for the inspection of materials and determining the quality of objects in other fields, e.g. geophysics, to the field of medicine.

At the present time medical applications of ultrasound for measuring parameters of bone tissue generally employee the direct transmission method in which a transmitter of ultrasonic oscillations and a receiver are disposed on opposite sides of the object being inspected. The known ultrasonic methods do not provide the required sensitivity in case of heterogeneous object such as bones. They demonstrate an integral approach based on averaging the obtained parameters such as amplitude or travel time and do not take into account situations in which the value of a parameter of the heterogeneous object being inspected is not uniform and increases in one part of the region through which the measuring beam travels and simultaneously decreases in another part.

The present invention uses an approach similar to that of the known geophysical tomographical method, which provides inspection from one side of the object only by means of non-linear propagation of ultrasound waves. The aforesaid method is applicable for inspecting heterogeneous objects contained in layered systems that are characterized by an acoustic impedance gradient. The method provides the possibility of unilateral inspection of heterogeneous media; however as applied in geophysics, this method gives integral results.

FIG. 1 schematically depicts the principle of the Geophysical Tomographical method for a layered system characterized by an elastic wave velocity gradient and containing heterogeneous objects.

The basis of this approach is the non-linear manner in which elastic waves propagate in systems comprising layers, which have an acoustic impedance gradient and which contain localized volumes of heterogeneous media (as local heterogeneous) (depicted as inclusions $1$ in an object $6$ being inspected). Inspection system $60$ comprises transducers $R_1$ to $R_{10}$ arranged along a linear profile on the surface $7$ of object $6$. The transducers $T_1$ and $T_2$ are situated at the opposite ends of surface $7$ of the layered system. Transducers $T_1$ and $T_2$ are used for transmitting sound wave as well as receiving sound waves. The geophysical method utilizes transducers aimed at right angle (90 degrees) to the surface of the observed object.

The non-linear wave propagation through this system results in curved routes of waves propagating from Transducer $T_1$ (activated as a transmitter) to the transducers $R_1$-$R_{10}$ and to Transducer $T_2$ (activated as a receiver) and are depicted in FIG. 1 by the solid lines $2$. Reciprocal routes, from transducer $T_2$ toward receivers $R_{10}$ to $R_1$ and to transducer $T_1$ are depicted by dashed lines $3$.

The fact of non-linear routes traveled by the beams is known from the literature and is similar to the propagation of light beams in heterogeneous media. If the media is characterized, for example, by a temperature gradient and the phenomenon is known as "a mirage" and is expressed by the fundamental Fermat principle. Similarly to light beams, elastic waves change their linear routes and traverse the route that offers the fastest time of travel.

The geophysical method is described, for example, in the work "Ore seismic" by N. A. Karaev and G. Ya. Rabinovich.—Moscow: Geoinformmark Closed Joint-Stock Company, 2000.—366 p, ill., and by L. A. Pevzner, V. L. Pokidov, V. A. Tsimer in the work "The seismic investigation of complex medium". Alma-Ata. Science, 1984. The geophysical method is not applied in medicine as it can not provide the needed resolution and sensitivity for medical investigations.

The geophysical method is based on the physical principles describing the propagation of an elastic wave through a layered system that is characterized by an acoustic impedance gradient and includes heterogeneous media. In accordance with the invention, parts of the human body to be inspected are considered to be such a layered system.

Similarly to the geophysical method, the invention considers the object being inspected as a local heterogeneous region in a human body or in an artificially created layered system and employs ultrasonic waves with wavelengths that are comparable in size to the dimensions of the local heterogeneous region.

The present invention applies a method of non-linear wave propagation for inspection of heterogeneous media similar to that of the geophysical method; however the method of the invention uses a differential approach to data measuring and treatment as opposed to the integral approach of the geophysical method. The method of the invention provides unilateral object volume inspections. The differential approach to data measuring and treatment of the invention provides sufficient sensitivity for the inspection of heterogeneous materials to allow the method to be applied to, for example, in vivo measurements of bones. The data corresponding to each element of a plurality of elementary volumes of the object that is provided by the differential approach of the invention are synthesized into 2D and 3D quantitative-images mapped according to a tomographical pixel-by-pixel approach.

The present invention is based on modification of and integration of the above described geophysical method with ultrasonic computer tomographical methods for simultaneously measuring and imaging. The sensitivity and ability to apply the tomographical method are made possible by the invention's use of the differential approach. This approach provides data for each elementary volume of an inspected layered system including local heterogeneous regions and it excludes the systematic and cumulative measurement errors caused by the presently used integral methods.

The invention uses the Time of Flight Diffraction (TOFD) technique to provide information about the upper layer and the geophysical method to obtain information about the layers beneath the upper one. The apparatus of the invention is adapted to emit ultrasonic oscillations at a constant angle $\alpha$ with respect to the surface of the inspected region and to receive the oscillations at a constant angle $\alpha$+ninety degrees with respect to the surface. In contrast to the geophysical method where this angle is ninety degrees, in the present invention the angle may be an acute angle to allow better penetration of the refracted waves into the object being inspected. A typical angle $\alpha$ might be, for example, forty-five degrees.

In an embodiment of the present invention transducers are arrayed on straight lines with a constant distance between transducers. The array of transducers can by arranged in a two dimensional grid or as a line of transducers that is moved parallel to the first line with constant step, equal to the distance between transducer in the line. Each transducer in the array can be activated as a transmitter or a receiver. The array of transducers is placed on the top of the layered surface, e.g. on the skin of a patient or a special additional layers placed over the object being inspected. The travel times in a system having a gradient of acoustic impedance and containing of heterogeneous mediums are measured by the following steps:

1) In the first step the correct magnitude of low frequency ultrasonic oscillations to be used with the transducers and the arrangement of the transducers for the inspection in a specific application must be determined. Firstly, the frequency must be chosen such that the length of the applied oscillations must be comparable to the dimensions of the inspected heterogeneous object, and secondly the distance between the first and last transducer must be much greater than the dimensions of the inspected heterogeneous object. For example a human vertebra has a dimension of 3 to 6 cm and the applied frequency is chosen to be approximately 100 kHz and the distance between first and last transducer should be greater than about 60 cm.

2) The first transducer in the line transmits ultrasonic oscillations in the direction of a body part being observed at an angle less than 90 degrees, e.g. 45 degrees. Elastic waves travel through the observed system containing an acoustic impedance gradient by non-linear routes. Beginning with the transducer located a distance $2\lambda$ to $3\lambda$ from the transmitter ($\lambda$ is the wavelength of the applied oscillations) each transducer of the remaining transducers in the array receive ultrasonic oscillations, which have passed through the object under investigation and the fastest time of travel between each transmitter-receiver pair is determined and stored for later use.

3) The measurements are repeated sequentially changing the distance between transmitter and receivers by a fixed distance equal to the distance between transducers each time. For example, if the measurements are made using a line of n equally spaced transducers, then after step 2 is completed with the first transducer as transmitter, then the second, third, fourth, etc. transducers are activated as a transmitter and the other transducers as receivers with the condition that the transmitting transducer must be located at a distance of more than about $2\lambda$ to $3\lambda$ from a receiving transducer.

4) The measurements of steps 1 and 2 are repeated in the reciprocal direction the needed number of times.

5) The line of transducers is now moved parallel to the original line (or a second line of transducers in a 2D grid is activated) and the measurements are repeated in the direct and reciprocal directions until data is obtained from each line in the transducer grid.

6) In order to use the differential approach of the invention, the volume of space containing the layered system is virtually divided into elementary volumes situated in columns and rows.

7) The data for the travel time between each transmitter-receiver pair is now analyzed to determine fastest travel times of the longitudinal wave signal through each elementary volume.

8) The values of the changes in the longitudinal wave travel time $\Delta t_m$ are determined in each volume (elementary volume) relative to volume located above it. The value of $\Delta t_m$ is determined from average values of the longitudinal wave travel times for adjoining routes in direct and reciprocal directions according to the formula $\Delta t_m = t_m + t_{m-1} - t_{dir} - t_{rec}$. Where $t_m$ is the average value of longitudinal wave travel time for direct and reciprocal directions for one transducer arrangement (where m is a number representing a transducer's location, i.e. 1, 2, 3 ... to ... m, from point m to point (−)m; $t_{m-1}$ is an average value of longitudinal wave travel time for direct and reciprocal directions for the transducer arrangement from point (m−1) to point (−m+1); $t_{dir}$ is an average value of longitudinal wave travel time for direct and reciprocal directions for the transducer arrangement from point (−m) to point (m−1) and $t_{rec}$ is an average value of longitudinal wave travel time for direct and reciprocal directions for the transducer arrangement from point m to point (−m+1).

9) The values of longitudinal wave travel times are determined for each elementary volume in each virtual vertical column of volumes by using the known (or previously measured) value of the longitudinal wave travel time $t_1$ in the first elementary volume from the surface and by successively adding the changes of the longitudinal wave travel times ($\Delta t_2$, $\Delta t_2$, $\Delta t_4$ ... $\Delta t_m$) for the elementary volumes below the first one in the column. This yields: $t_2=t_1+\Delta t_1$; $t_3=t_2+\Delta t_2$ ... and $t_m=t_{m-1}+\Delta t_{m-1}$.

10) The average longitudinal wave velocity values in an each elementary volume are now determined from the values of the shortest longitudinal wave travel times in each elementary volume determined in the previous step and the length of travel of the longitudinal wave in each elementary volume. The length of travel of the longitudinal wave in each elementary volume is approximated by assuming that the longitudinal waves travel the same distance in each of the elementary volumes beneath the elementary volumes of the first layer of layered system. This distance is half the circumference of a circle having radius b, where b is the distance between adjoining transducers, i.e. πb. The wave travels in straight lines through the elementary volumes of the first layer; therefore the length of travel time in the known first layer is 2b/sin α where α is the incident angle on the first layer or $2\sqrt{2}*b$ if the 45 degrees.

11) Statistical treatment is now applied to the obtained longitudinal wave velocity values to determine the value of the longitudinal wave velocity in the matrix (skeleton) mineral part of an observed material $V_t$. The material matrix part is solid and the strongest part of an inspected material. This part of the object corresponds to elementary volumes that have the maximum values of longitudinal wave velocity from the range of values of velocities obtained for all of the elementary volumes of the inspected object and is determined by statistical treatment of the results of the previous step.

12) The values of porosity n for each elementary volume of an observed volume of space are calculated by the modified Wyllie relationship from oil geophysics. (Wyllie, M. R., An experimental investigation of factors affecting elastic wave velocities in porous media, Geophysics, vol. 23, No. 3, 1958):

$$n=((V_t-V_p)*V_{fill})/V_p*(V_t-V_{fill}))$$

Where $V_p$ is the calculated values of the longitudinal wave velocity in an elementary volume, $V_t$ is the true value of a longitudinal wave velocity in a matrix (skeleton) mineral part of an observed material, $V_{fill}$ is a longitudinal velocity value in a filling, i.e the material in the pores, of an inspected media.

13) Images (maps of horizontal or vertical 2D sections are repeated along the third axis with a constant step for 3D imaging) of longitudinal wave velocity and porosity values distributions are built pixel-by-pixel by applying programs such as "Excel" or MatLab from the data for the elementary volumes from which an inspected volume is composed. The calculated values for the elementary volumes are written in a table of columns of elementary volumes that repeat with constant step. The constant step between the columns in the sequence of the columns corresponds to the distance between transducers. The table is applied for images building.

14) Analysis of the obtained maps reveals physiologically distinctive areas in the inspected object; reveals problematical zones, i.e. the zones with fracture risk, their dimensions and locations; and gives an estimate of the magnitude of the risk. This information is revealed by observing decreases in the values of the elastic wave velocities and increases in porosity values that are shown in different areas of the images of the observed bone of a human body. Estimation of and revealing the location of risk of fracture in these maps of the inspected object is realized by calculating the ratio of relative changes of the longitudinal wave velocity values for the area divided by the longitudinal wave velocity in the material matrix of the object.

15) In addition to the two parameters that determine a bone structure, i.e. bone mineral skeleton and bone porosity, the statistical treatment of the data is carried out to provide information about other internal organs of an individual and to reveal changes in properties of the organs, such as their dimensions.

The 3D measuring-imaging Ultrasonic Tomographical method of the invention is adaptable to investigations of almost all the bone types and structures in a human body, e.g. cortical bone, trabecular bones, and marrow in bones, as well as surrounding soft tissue.

FIGS. 2A and 2B schematically illustrate the difference between the integral approaches of the currently used ultrasonic methods and the differential method of the invention.

FIG. 2A schematically shows the set up of the methods currently applied to inspection of heterogeneous and anisotropic material. An ultrasonic transmitter (T) located at one side of the object (region) being inspected transmits an ultrasonic wave to the receiver (R) at the other side of the object. The figure shows how the integral approach results in data averaging of the signals as they travel from the transmitter to the receiver. The averaging takes place because the value of a parameter being measured may increase in one part of the object and be reduced in another part of it as the wave travels across the medium and the changes can not be revealed by applying integral approach. The same result is obtained using Pulse-Echo, TOFD, and other known methods for inspecting heterogeneous media. The observer travel times or amplitudes are averaged over the distance the signals travel through the media and as a result the observed parameters are not sensitive enough for imaging of the structure being investigated.

FIG. 2B shows the principle of the differential approach of the invention. According to this approach the volume of an object being inspected is divided into smaller sub-volumes called elementary volumes. The measurements and data treatment provide data for each elementary volume of the inspected object and images are constructed from the data obtained for each elementary volume on a pixel-by-pixel basis thereby providing the sensitivity to the measurements and providing image mapping that takes into account the influence of the heterogeneity and anisotropy of the media being investigated.

FIG. 2C schematically depicts one vertical slice of the 3D observed volume of the inspected object as a 2D array of elementary pixels arranged in columns and rows. The locations of the transducers $S_1$ ... $S_m$ are shown also in the figure.

For simplicity, one vertical slice of the observed three-dimensional (3D) object is depicted in FIG. 2C. Volume (13) of the inspected object is considered as a plurality of elementary volumes (cubes in 3D). The distance between transducers ($S_1$, $S_2$, $S_3$ ... $S_{m-1}$, $S_m$) on surface 19 of the object 13 is constant and is equal to b. (Note that to obtain the full 3D image the transducers are arranged in a 2D matrix on the surface of the object being examined and that the distance between adjacent transducers in both directions is b.) The value b defines a distance between the lines of the grid that in turn define the dimensions of the elementary volumes. The elementary volume of the first layer 12 of the layered system being investigated is indicated by a numeral $12_i$. According to the notation used herein pixel $12_3$ is the pixel in the first row that is directly underneath transducer $S_3$. The pixels in the rest of the rows of the slice are identified as pixel $13_{i,j}$ according to their row i and column j.

It is to be understood that a plurality of such two-dimensional (2D) slices may be combined to create a representation of the full 3D object. The pixel may be chosen as cubical having an elementary volume of $b*b*b=b^3$. In the depicted example, the vertical slice is in the X-Y plane, while adjoining slices may be spaced in the Z direction with a constant step which is equal to b. This method of 3D bone imaging by means of integrating a plurality of 2D images will be described further with reference to FIG. 15, which depicts 3D imaging of experimental results.

According to the method of the invention the object to be investigated may be larger than the size of the transducer array since, for a given number of transducers any number of slices, and any number of columns and rows may be obtained by moving the transducer array from one location to another on a virtual grid on the surface of the layered system.

It is desirable that the depth of the penetration of the acoustic beams into an inspected body be as large as possible. This can be accomplished by applying low frequency oscillations; wherein, for a given situation, the frequency of the oscillations is chosen such that the length of the longitudinal ultrasonic wave $\lambda_{wav}$ in the medium is comparable to the dimension d of the object.

According to this condition, the preferred frequency for bone media inspections lies in the low range of frequencies of, for example, 25 to 100 kHz.

Existing ultrasonic devices for medical applications apply high frequency ultrasonic oscillations to generate linear beams of ultrasonic waves. The present invention employs low frequency ultrasonic oscillations and non-linear beam travel to inspect an object that is considered as a local heterogeneity in a layered system. The difference of the approaches may be seen from the FIG. 2D and FIG. 2E. Considering an analogy with light waves, light has a very small wavelength and high frequency, so only very small objects or gaps can effect its direction. Under these conditions the person in FIG. 2D can't see the three persons on the other side of the wall. In contrast to the light case, sound waves have relatively long wave lengths and low frequencies and bend round objects having dimensions similar to that of their wavelength. Thus the three persons in FIG. 2E can hear the person on the other side of the wall talking to them and vice versa even though they can not see each other. Existing medical devices act in a manner similar to the light waves shown in FIG. 2D. The present invention uses ultrasonic waves whose properties enable them to behave in a manner similar to sound waves as shown in FIG. 2E.

The entire volume is investigated by virtually dividing it into elementary volumes, selecting a vertical column, performing the calculations for the elementary volume closest to the surface followed by the sequence of the elementary volumes beneath it, and then selecting another vertical column and repeating the procedure. The acoustic properties of the uppermost elementary volumes should be known. This can be achieved by implementing the first layer of the system as an additional plate and/or pillow having known acoustic properties. For the human body the first layer of the system can be the skin which has known properties. The acoustic properties of the first layer may be calculated also, but one needs to take into account that the length of routes of elastic waves in the pixel of the first layer differs from the length of routes of elastic waves propagating through elementary volumes of other layers. Alternatively, the object may be immersed in a container with liquid having known acoustic properties. Immersion in liquid or use of a pillow filled with jell may be used for interfacing a generally curved surface, e.g. part of a human body, with the planar surface carrying the transducer array.

As previously mentioned the invention is based is on the fact that the human body can be considered to be a layered system comprising skin, fat, periosteum, cartilage, and muscle that is characterized by an acoustic impedance gradient. In this system bones are considered as localized heterogeneous bodies embedded in the layered system.

In other investigations a layered system may be artificially provided by attaching suitably configured additional layers or parts to the object that it is desired to study in order to cause the ultrasonic waves to propagate non-linearly in the resulting complex layered system.

Figure 3:
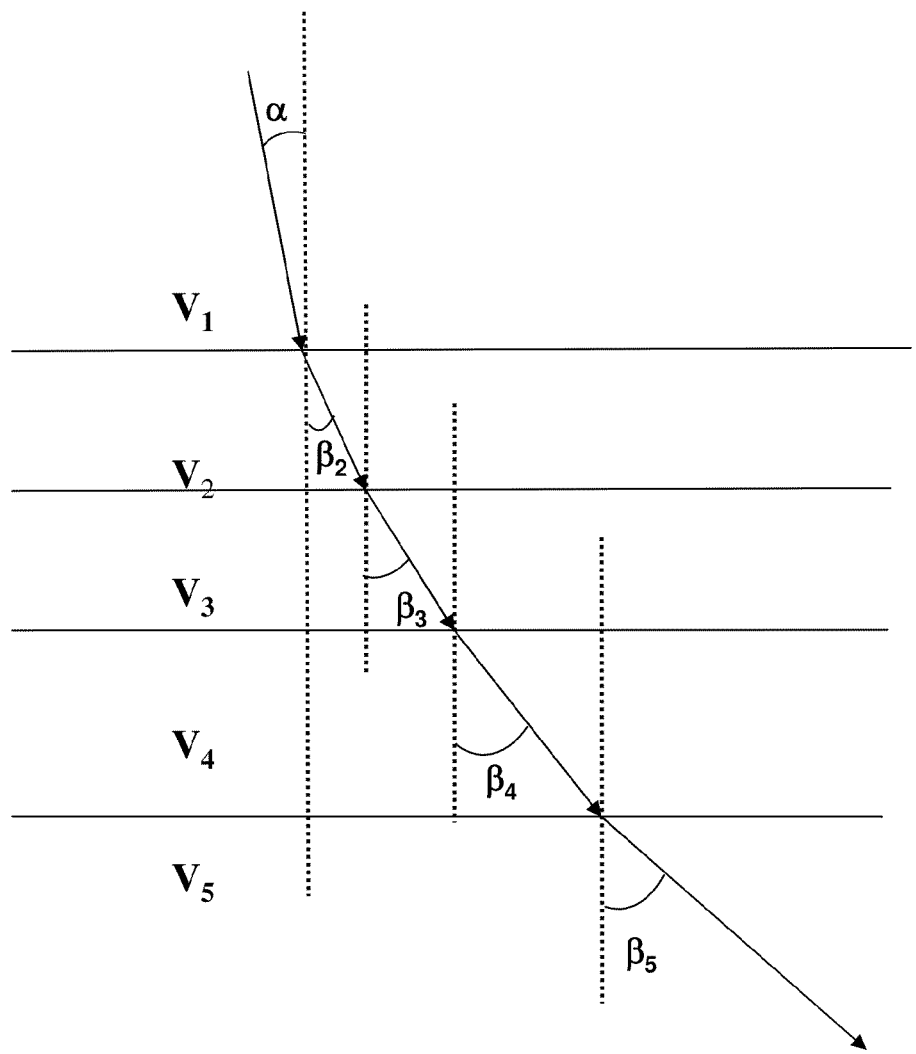
FIG. 3 schematically depicts a layered system characterized by an acoustic impedance gradient and the direction of elastic wave propagations in the layered object.
Figure 4:
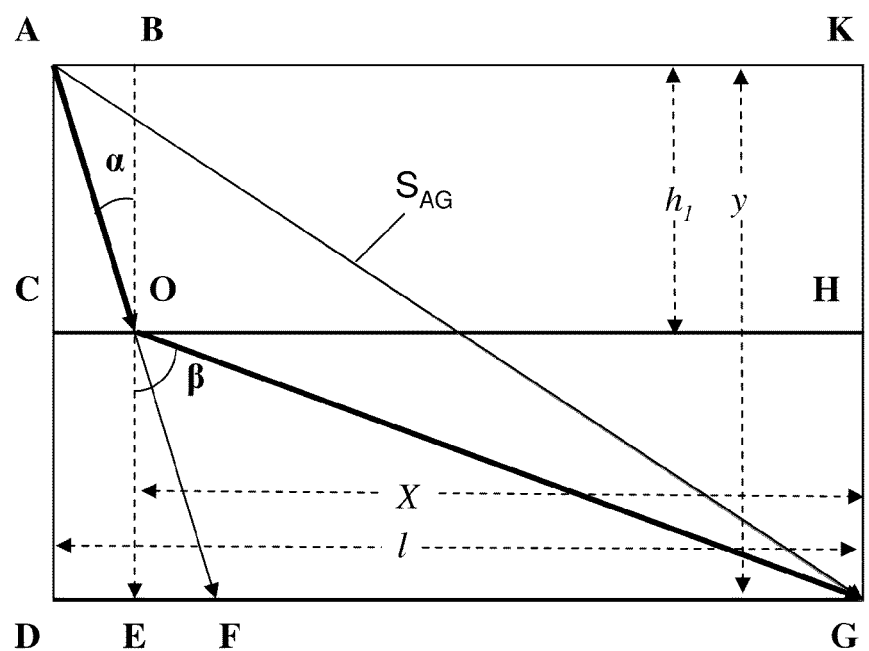
FIG. 4 schematically depicts some details of a multi-layered system comprised of layers with an acoustic impedance gradient that is considered to be equivalent to a two-layered system comprised of the first layer and the $n^{th}$ layer.

FIGS. 3, 4, 5 and 6A to 6D schematically explain the differential approach of the invention to data measurements and treatment of heterogeneous layered media that allows tomographical mapping of data corresponding to a plurality of elementary volumes. This approach provides the measurements with sufficient sensitivity (resolution) to be used, for example in medical applications. FIG. 3 and FIG. 4 illustrate the non-linear propagation of the ultrasonic beams in layered systems.

FIG. 3 schematically presents a layered system characterized by an elastic wave velocity (acoustic impedance) gradient. The direction that the beam travels in each layer is determined according to Snell's reflection law at each of the interfaces:

$$\sin \alpha / \sin \beta = V_A / V_B$$

Where $\sin \alpha$ is the sine of the incident angle on the boundary between two media A and B having different acoustic impedances and $\sin \beta$ is the refracted angle in the second media. $V_A$ and $V_B$ are the longitudinal wave velocities in the first and the second media for the case when the system consists of two layers.

In the example of FIG. 3, a system composed of five layers with gradient velocities that are expressed as:

$$V_1 < V_2 < V_3 < V_4 < V_5$$

According to Snell's refraction law for the boundary between media 1 and 2 of the system depicted in FIG. 3, the propagating wave will obey the following condition:

$$\sin \alpha / \sin \beta_2 = V_1 / V_2$$

This equation can be solved to yield:

$$\sin \beta_2 = \sin \alpha * V_2 / V_1$$

Similarly, for boundary 2 which is the boundary between media 2 and 3:

$$\sin \beta_2 / \sin \beta_3 = V_2 / V_3$$

Where $\sin \beta_2$ is the sine of the incident angle on the boundary between media 2 and 3, $\sin \beta_3$ is the refracted angle in the third medium, and $V_2$ and $V_3$ are the longitudinal wave velocities in the second and the third media.

$\sin \beta_3$ may be expressed as:

$$\sin \beta_3 = \sin \beta_2 * V_3 / V_2$$

and thus as:

$$\sin \beta_3 = \sin \alpha * V_3 / V_1$$

For boundary 3 between the media 3 and 4 we can write:

$$\sin \beta_3 / \sin \beta_4 = V_3 / V_4$$

Wherein $\beta_3$ is sine of the incident angle on the boundary between the media 3 and 4, $\sin \beta_4$ is the refracted angle in the fourth medium, $V_3$ and $V_4$ are the longitudinal wave velocities in the third and the fourth media.

sin $\beta_4$ may be expressed as:

$$\sin \beta_4 = \sin \alpha * V_4/V_1$$

And by analogy for the boundary n−1, which is the boundary between the media n−1 and n the relations may be written as:

$$\sin \beta_{n-1}/\sin \beta_n = V_{n-1}/V_n$$

And thus by analogy:

$$\sin \beta_n = \sin \alpha * V_n/V_1$$

Hence, a multi-layered system comprised of layers with an acoustic impedance gradient may be considered to be equivalent to a two-layered system comprised of the first layer and the $n^{th}$ layer.

FIG. 4 schematically depicts some details of a multi-layered system comprised of layers with an acoustic impedance gradient that is considered to be equivalent to a two-layered system comprised of the first layer and the $n^{th}$ layer.

The region AKCH represents the first layer and CHDG the $n^{th}$ layer of the layered system. The longitudinal wave velocities in the layers are depicted by $V_1$ and $V_n$ respectively. The distance AK=l, is half of the distance between a transmitter and a receiver for a transducer arrangement such as shown in FIG. 2C. The thickness of the first layer is $h_1$, sin $\alpha$ is the sine of the incident angle at the external boundary of the first layer and sin $\beta_n$ is the sine of the refracted angle in the medium n.

According to Snell's relationship for the layers:

$$\sin \alpha/\sin \beta_n = V_1/V_n$$

The expression $\sin \beta_n \times V_1 = \sin \alpha \times V_n$ describes an average velocity value for oscillations traveling from point A to point G along the paths AO and OG. According to Fermat's principle, ultrasonic oscillations travel along the fastest route.

Defining the distances: EG as x, and AD as y, and $S_{AG}$ is the shortest distance from point A to point G; $S_{AG}$ may be expressed as:

$$S_{AG} = (l^2 + y^2)^{1/2}$$

And thus the shortest travel time $\tau_{short}$ may be written as: $S_{AG}/(\sin \alpha \times V_n)$ or as:

$$\tau_{short} = ((l^2+y^2)^{1/2})/\sin \alpha V_n$$

$$\sin \alpha = (l-x)/((l-x)^2+h_1^2)^{1/2}; \sin \beta_n = x/(x^2+(y-h_1)^2)^{1/2}$$

therefore:

$$\sin \alpha/\sin \beta_n = ((l-x)*(x^2+(y-h_1)^2)^{1/2})/(x*((l-x)^2+h_1^2)^{1/2}) = V_1/V_n$$

$$\tau short = ((l^2+y^2)^{1/2}*(h_1^2+(l-x)^2)^{1/2})/((l-x)*V_n)$$

Similarly, the shortest time may be written as the corresponding distances divided by the corresponding velocity values: $S_{AO}/V_1 + S_{OG}/V_n$ or as:

$$\tau short = (h_1^2+(l-x)^2)^{1/2}/V_1 + (x^2+(y-h_1)^2)^{1/2}/V_n$$

The equation for the shortest time can be expressed as:

$$((l^2+y^2)^{1/2}*(h_1^2+(l-x)^2)^{1/2})/((l-x)*V_n) = (h_1^2+(l-x)^2)^{1/2}/V_1 + (x^2+(y-h_1)^2)^{1/2}/V_n$$

Dividing both parts of this equation by $(h_1^2+(l-x)^2)^{1/2}$ yields:

$$(l^2+y^2)^{1/2}/((l-x)*V_n) = 1/V_1 + ((x^2+(y-h_1)^2)^{1/2})/(((l-x)^2+h_1^2)^{1/2}*V_n))$$

The equation may be written for direct and reverse directions as:

$$(l^2+y^2)^{1/2} = ((l-x)*V_n)/V_1 + (V_i*x)/V_n;$$

$$y^2 = ((l-x)^2*V_n^2)/V_1^2 + 2lx - x^2 - l^2 + (V_1^2*x^2)/V_n^2;$$

$$y2 = (l-x)^2|V_n^2/V_1^2 - 1| + x^2|V_1^2/V_n^2 - 1|;$$

or $$y2 = (l-x)^2|\sin^2 \beta_n/\sin^2 \alpha - 1| + x^2|\sin^2 \alpha/\sin^2 \beta_n - 1|$$

Therefore the maximal depth of beam penetration for the refracted wave is determined by the gradient velocity values $(V_n/V_1)$ of the media and by the distance between a transmitter and a receiver 2l. Hence, a system for Ultrasonic Tomographical measurements may be based on changing of the distances between transmitting and receiving transducers which are situated at one surface of a layered system being investigated.

The proposed Ultrasonic Tomographical measurements are based on changing the distance between transducers acting as transmitters and as receivers which are situated at a distance of more than two to three wavelengths of the applied oscillations on one surface of the layered system being inspected.

Figure 5:
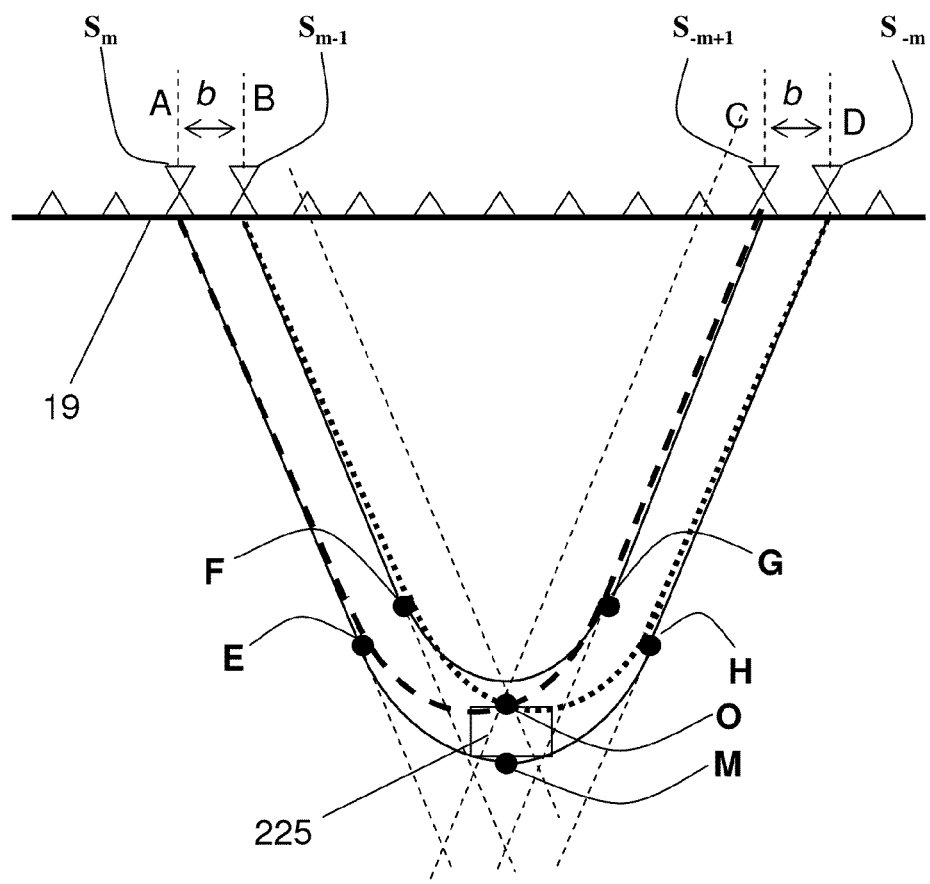
FIG. 5 demonstrates the direct and the reciprocal routes of propagating elastic wave for adjacent locations in the vertical slice according to the applied algorithm according to the invention.

FIG. 5 schematically shows the direct and the reciprocal routes corresponding to each combination of elastic waves propagating from a pair of adjacent transmitting transducers to a pair of adjacent receiving transducers through a selected elementary volume in the vertical slice. The figure shows the measurement system of the invention and the propagation of the elastic waves through the layered system.

Transmitters (or transceivers activated as transmitters) located at points A and B emit ultrasonic oscillations at an angle to the surface 19 of the system being investigated. The oscillations are received by receivers (or transceivers activated as receivers) that are situated at locations C and D which are oriented at the same angle plus ninety degrees, i.e. the transmitters are oriented at an angle $-\alpha$ with respect to the normal to the surface and the receivers are oriented at an angle $+\alpha$ with respect to the normal to the surface.

Four routes may be plotted in the direct direction from transmitters A and B to receivers C and D: AC, AD, BC, and BD.

Similarly, if the transducers at C and D are made the transmitters and those at A and B the receivers, then four routes in the reciprocal direction at obtained: CA, DA, CB, and DB.

The invention utilizes an algorithm, which provides a differential approach to measurement and treatment of the obtained data. The proposed algorithm, which is based on addition and subtraction of the longitudinal wave travel times for selected combinations of the direct and reciprocal routes associated with adjacent locations is explained by referring to FIGS. 6A to 6D. It should be noted that the orientation of the emitted and received beams such as depicted by lines AE, BF, GC, and HD is preferably 45 degrees to surface 19; however, smaller or larger angles can be used.

If the average values of the longitudinal wave travel times for longitudinal wave propagation along the routes in direct and reciprocal directions between a two adjacently points A-D and B-C are added and the corresponding average values of the longitudinal wave travel times between points A-C and B-D subtracted, then the differences for the travel times through a considered elementary volume relative to the elementary volume located above it in the column being considered is obtained.

FIG. 6A to FIG. 6D relate to the measurement system shown FIG. 5. These figures show details of the elementary volume selection and explain the algorithm of the invention that is used to determine the changes in the value $\Delta t_m$ of the travel time of the acoustic wave through each elementary volume relative to the elementary volume above it in the same column within the layered system. The figures corresponds to the transducer arrangement with step b on the surface 19 and show how the difference in travel times $\Delta t_m$ for the elementary volume 225 is determined relative to the previous elementary volume, i.e. the elementary volume above it along on the vertical axis passing through the points O and M.

The prior art methods, including the geophysical method, consider only signals from two transmitted beams for selection of the part of an object being inspected. In contrast, the method of the invention employs a minimum combination of signals from four beams transmitted in either the direct or the reciprocal direction to determine the properties of a specific elementary volume in the observed object. Embodiments of the method that give more accurate results employ a combination of signals from eight transmitted beams to determine the properties of a specific elementary volume in the observed object.

Referring to FIGS. 6A to 6D the method for determining the difference of the obtained average travel times for signals traveling in direct and reciprocal directions between points A, B, C, D through elementary volume 225 will now be explained.

Figures 6A, 6B, 6C:
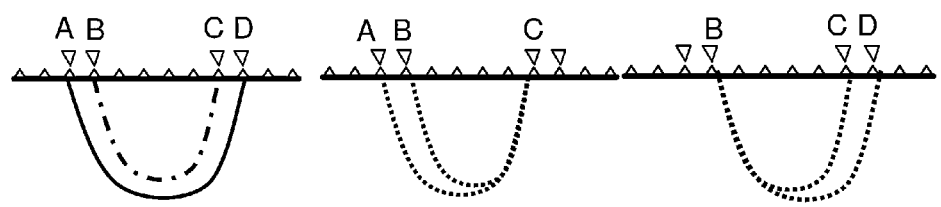
FIGS. 6A to 6D demonstrate the method for determining the difference of the obtained average travel times for signals traveling in direct and reciprocal directions through a selected volume.
Figure 6D:
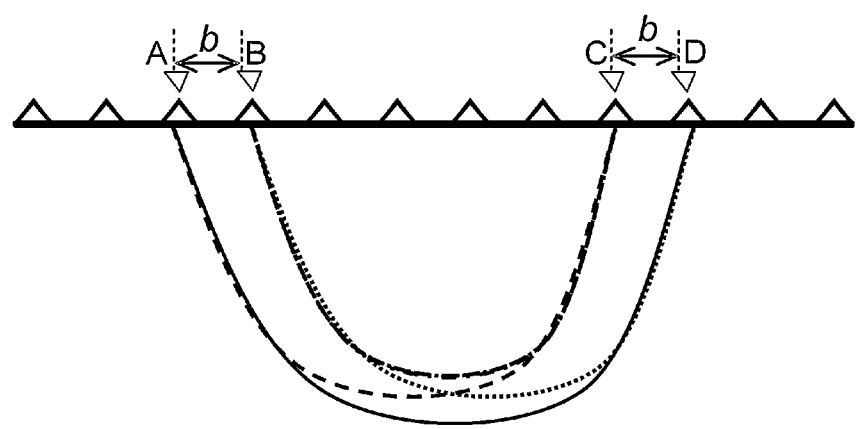

The measured difference of the average time it takes the signal to travel between points A-D and B-C $t_{AD}$-$t_{BC}$ is graphically represented by the arcs seen in FIG. 6A. Consider the difference of measured average times for signal traveling between points A-C and points B-C. The obtained difference $t_{AC}$-$t_{BC}$ is represented by the arcs shown in FIG. 6B. Consider the difference of measured average times for signal between points B-D and points C-B. The obtained difference $t_{BD}$-$t_{CB}$ is represented by arcs shown in FIG. 6C.

Subtracting FIG. 6B and FIG. 6C from FIG. 6A, results in the difference between the average travel time across elementary volume 225 in FIG. 5 relative to the average travel time across the elementary volume above it on the same vertical axis. The changes of the travel times $\Delta t_m$ between a considered elementary volume relative to the elementary volume above it may be expressed:

$$\Delta t_m = (t_{AD} - t_{BC}) - (t_{AC} - t_{BC}) - (t_{BD} - t_{CB}) = t_{AD} + t_{BC} - t_{AC} - t_{BD}$$

Referring to FIGS. 6A to 6D, $\Delta t_m$ is the difference between the smallest travel time for ultrasonic oscillations along the curvilinear routes through elementary volume 225, i.e. ($t_{EM}$+ $t_{MH}$) and through the elementary volume above it. i.e. ($t_{EO}$+ $t_{OH}$). Thus $$\Delta t_m = t_{AE} + t_{EM} + t_{MH} + t_{HD} + t_{BF} + t_{FO} + t_{OG} + t_{GC} -$$
$$t_{AE} - t_{EO} - t_{OG} - t_{GC} - t_{DH} - t_{HO} - t_{OF} - t_{FB}$$
$$= t_{EM} + t_{MH} - t_{EO} - t_{OH}$$

The calculations for the average velocity value of a longitudinal wave for each elementary volume are carried out by using the known values of longitudinal wave travel time in the first elementary volume of a column under consideration, adding the value of $\Delta t$ determined according to the equations above for the second elementary volume, and determining the length of travel through the elementary volume. This gives a result for the second elementary volume in the column. The process is now repeated for each successive descending elementary volume in the column and for each column in the system being studied.

From the above, the average time of travel of the longitudinal wave through the elementary volume is known. In order to determine the distance that the wave travels through the elementary volume the multi-layered system is considered as if it has been replaced with an equivalent system constituting of two layers according to equation $\sin \alpha / \sin \beta_n = V_1 / V_n$ as discussed above with relation to FIG. 3. The known first layer of the system is the first layer of the equivalent two layer system and the second layer of the two level system is the layer that contains the elementary volume under consideration. The travel length through an elementary elementary volume is defined by an estimated value, calculated as half of the circumference of a circle with radius b, that is length=$\pi$*b. It is assumed that the length of travel through the first known layer is $2b/\sin \alpha$, where, $\alpha$ is the angle of incidence with the layered system and b is the distance between transducers.

Since, using the above, both $\Delta t$ and the length of the path of the wave through each elementary volume can be determined the velocity of the elastic wave which travels through each elementary volume can easily be determined.

Figure 7A:
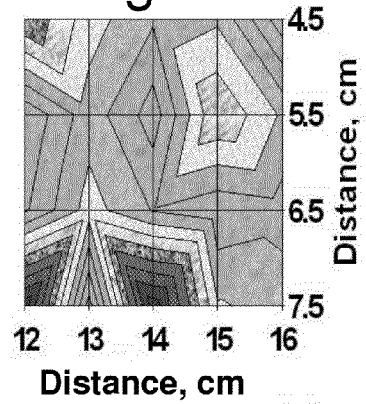
FIGS. 7A and 7B show experimental results obtained using the differential method of the invention in a system comprised of bone and surrounded by soft tissues.
Figure 7B:
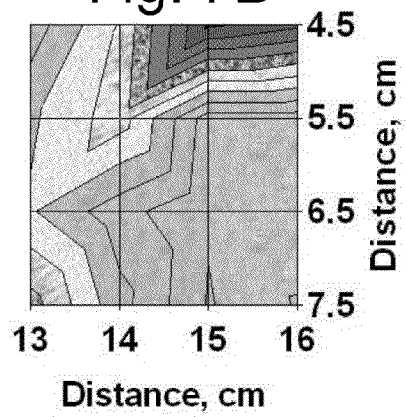
Figure 7C:
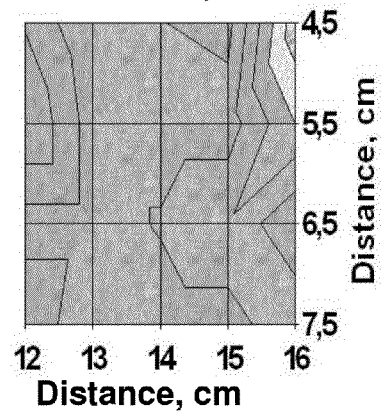
FIGS. 7C and 7D show experimental results obtained using the prior art integral method in a system comprised of bone and surrounded by soft tissues.
Figure 7D:
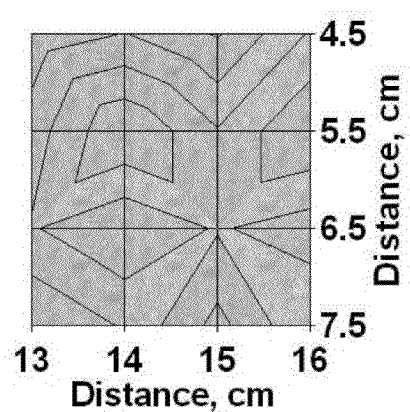

FIG. 7A to FIG. 7D present experimental images showing the values of the longitudinal wave velocity in a 2D slice for a system including a bone with a cut at 6.5 cm and surrounding soft tissues. FIGS. 7C and 7D were obtained by means of the integral approach as described in U.S. Pat. No. 6,221,019 and U.S. Pat. No. 5,143,072 (see background) and they demonstrate the insensitivity of the aforesaid approach to local changes of the longitudinal wave velocity within the inspected object and do not reveal the bone and the boundary between bone and soft tissue. FIGS. 7A and 7B are for the same system and the same specimen but were obtained using the differential approach of the invention.

The majority of known methods used for measuring the wave velocity in the majority of applications use the integral approach that does not provide the possibility for inspecting heterogeneous materials (such as bone) with sufficient sensitivity. The obtained experimental results that are shown, for example, in FIG. 7A and FIG. 7B demonstrate the improved sensitivity of the proposed differential approach of the invention.

FIGS. 8A to 8D and 9A to 9D schematically depict the method of data acquisition according to the current invention: FIG. 8A to FIG. 8D schematically depict a succession of measurements in the direct direction and FIG. 9A to FIG. 9D schematically depict a succession of measurements in the reciprocal direction. For simplicity a 1D array of transducers is shown. Extension of the method to a 2D transducer array is done by activation of each row of transducers either in series of simultaneously with some or all of the other rows.

According to an embodiment of the invention, an electronic signal is transmitted from the scanning controller 39 to one of the transducers $S_i$ in the row of transducers 26 which is in contact with the surface 19 of the observed object 27 having internal structure 29.

Figures 8A, 8B:
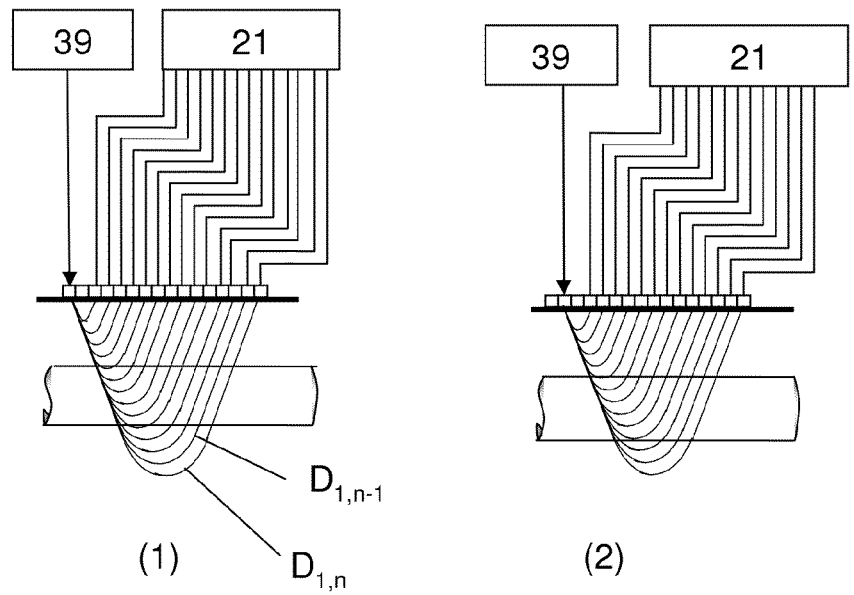
FIGS. 8A to 8D and 9A to 9D schematically depict the method of data acquisition according to the current invention.

FIG. 8A depicts the situation in which the first transducer $S_1$ in the row is used as a transmitter. The first transducer $S_1$ is angled to the right by using a wedge or other angulation means. The paths of acoustic beams from transducer $S_1$ to other transducers in the line are shown. These transducers are used as receivers and are angulated to the left along the marked paths the same number of degrees from the normal to surface 19 as is $S_1$. Direct paths are marked as $D_{ij}$ wherein i is the index of the transmitter and j is the index of the receiver.

Electronic signals from the receivers are transmitted to the time measuring unit 21 which detects and measure the arrival time of acoustic signal to the transducer, thus determining the time of flight from transducer i to transducer j along the direct path $D_{ij}$, which is the time t. For simplicity, only $D_{1,n}$ and $D_{1,n-1}$ are marked in FIG. 8A. Measuring time unit 21 may process the signal from one transducer at a time or may be a processing unit capable of parallel processing a plurality of signals from other transmitter-receiver pairs at the same time.

In FIG. 8B, the second transducer $S_2$ in the line is used as a transmitter and remaining transducers as receivers. The transducer $S_2$ is angled to the right by using a wedge or other angulation means. The paths of the acoustic beams from transducer $S_2$ to the other transducers acting as receivers are shown in the drawing. The beams arrive at the other transducers along the curved lines, which are angulated to the left along the marked paths. The transducer $S_1$ is idle when $S_2$ is activated.

Figures 8C, 8D:
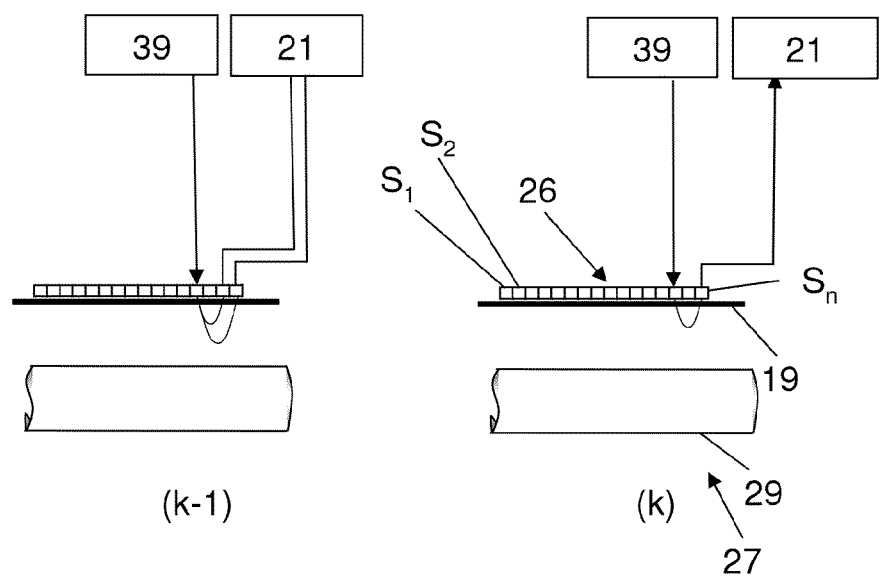
Figures 9A, 9B:
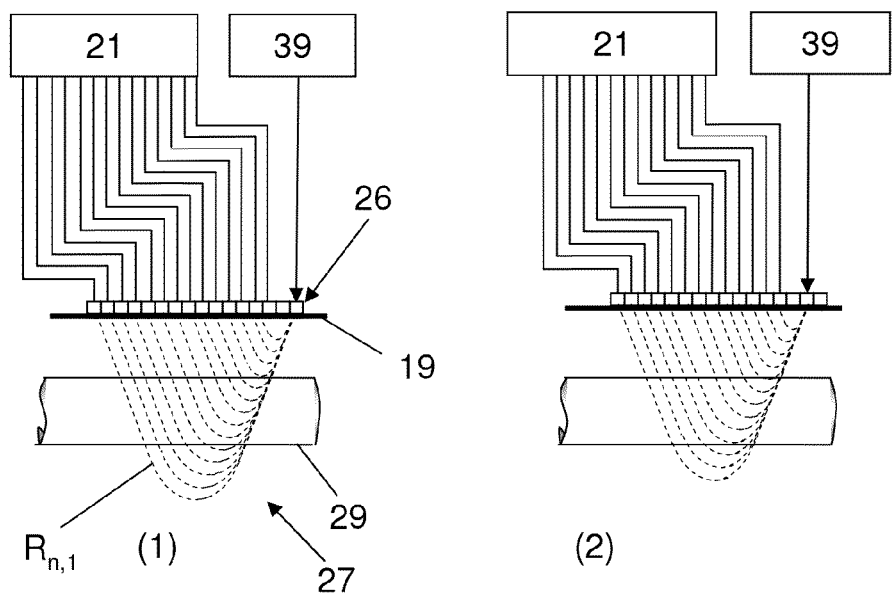
Figures 9C, 9D:
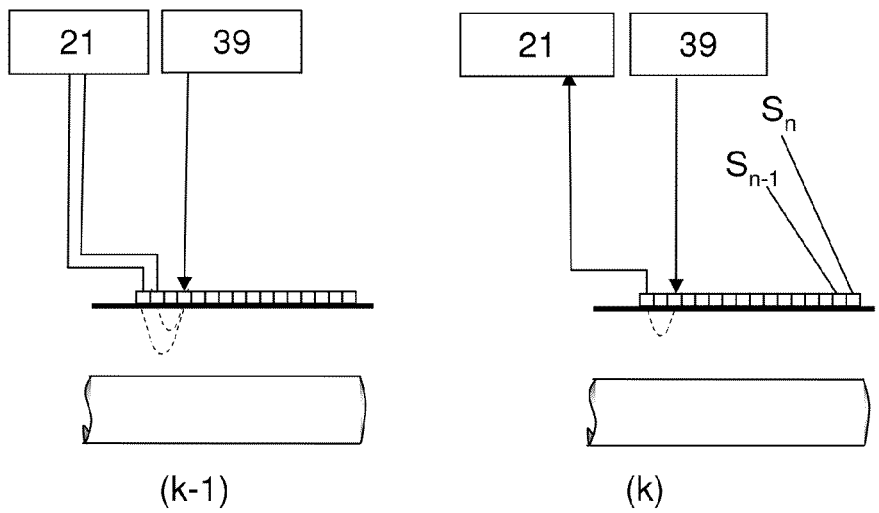

The measurement process repeats until most of the transducers are used as transmitters. FIG. 8C and FIG. 8D show the situation when transducers (k−1) and (k) respectively are used as the transmitters, wherein k is smaller than the number of transducers in the array n since generally the same transducer is not used as both transmitter and receiver at the same time. In fact a minimal gap equal to about 2 to 3 wave lengths of the applied oscillations must be maintained between transmitter and receiver.

Reciprocal paths $R_{i,j}$ are similarly marked in dashed lines in FIGS. 9A to 9D, which show transducers (1), (2), (k−1) and (k) respectively activated as transmitters. For measuring reciprocal paths, the receivers are angulated to the right while the transmitters are angulated to the left.

It is understood that the sequence of measurements may be varied. It may be changed systematically or even randomly within the same row or among the rows and columns in a 2D array. However, it is preferred that all transmitter-receiver pairs in each line would be measured at least once.

Figure 10:
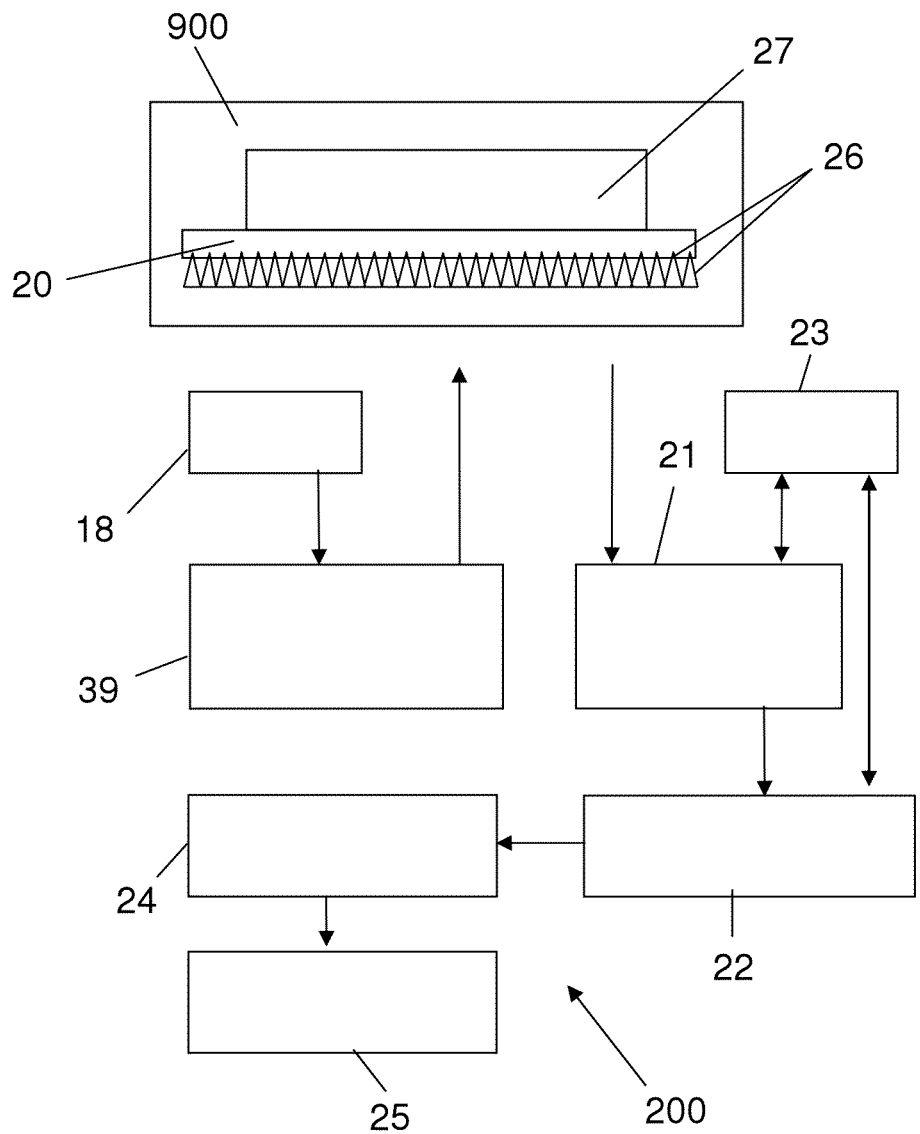
FIG. 10 schematically depicts a functional block diagram of the ultrasonic tomography device according to an embodiment of the current invention.

FIG. 10 schematically depicts a functional block diagram of the Ultrasonic Tomograph according to an embodiment of the current invention. Ultrasonic Tomograph 200 is used to measure objects 27 such as parts of a human patient and to obtain a map of structural features and the distribution of properties of the materials in the observed object. Additionally, tomograph 200 may detect fractures and reveal the location of bone weaknesses and in this way estimate the risk of bone fracture.

Signal generator 18 produces electronic signal in the form of short pulses. The generated signal is directed by a scanner position controller 39 to the transducers 26 of the three dimensional ultrasonic system 900. In the figure an additional plate 20 of material is shown located between the object 27 and transducers 26. Plate 20 is introduced to create the layered system with an acoustical impedance gradient.

Scanner position controller 39 also controls the orientation of transducers 26. As described herein above, the transmitters are oriented at an angle that "points towards" the receiver in order to receive the signals. For example a transmitting receiver may be oriented at a 45 degree angle relative to the surface of the volume being inspected in which case the receiving transducers are oriented at an angle of 135 degrees. In order to change the mode of a transducer from that of transmitter to receiver it is necessary to change its orientation from 45 degrees to 135 degrees and vice versa. There are many ways known in the art to accomplish this, for example, the transducer 26 at each location may actually be comprised of two transducers each pointed in one of the two required directions. Alternatively, scanner position controller 39 may control electro-mechanical devices such as solenoids (not shown), which are part of the transducer set 20 system, for changing the orientation of the individual of transducers 26. In addition in embodiments of the invention the area of the transducer set may be smaller than the surface area of the region to be investigated. In this case transducer set 20 can be mounted on a framework and scanner position controller 39 may control an electro-mechanical device such as a stepper motor (not shown) to move transducer set 20, thereby scanning the array of transducers over the surface of the observed object 27.

Signals from transducers 26, indicative of received ultrasonic signals are directed from each of the receiving transducers to a time measuring unit 21. Unit 21 receives the signals, amplifies, filters, and processes them to measure the shortest travel times along the direct and reciprocal paths. The measured travel time, in digital format is transferred to signal processor 22 which uses the algorithm disclosed herein above to determine the differential data and stores the data in a storage device 23. In different embodiments the storage device 23 can be, for example a digital memory or a data storage disk Storage device 23 may serves other digital units such as processor 22 and/or an image formation unit 24 in addition to signal processor 22.

Image formation unit 24 uses the obtained data associated with plurality of elementary volumes for pixel-by-pixel image mapping of the distribution of properties of the object, e.g. bone that is being inspected. The image formation unit 24 is also adapted to analyze the maps that have been obtained. Amongst other things, the analysis may include interpretation of the obtained images to reveal physiological details of distinctive zones of the inspected object. The results of the mapping and/or analysis are displayed on a display unit 25.

It should be noted that the functions of the processor 22 and image formation unit 24 may be combined in a single device, for example a general purpose computer such as a PC or a laptop. The processing and image formation software may be programmed in any one of a several suitable computer languages such as C++, Excel or MatLab.

Figure 11:
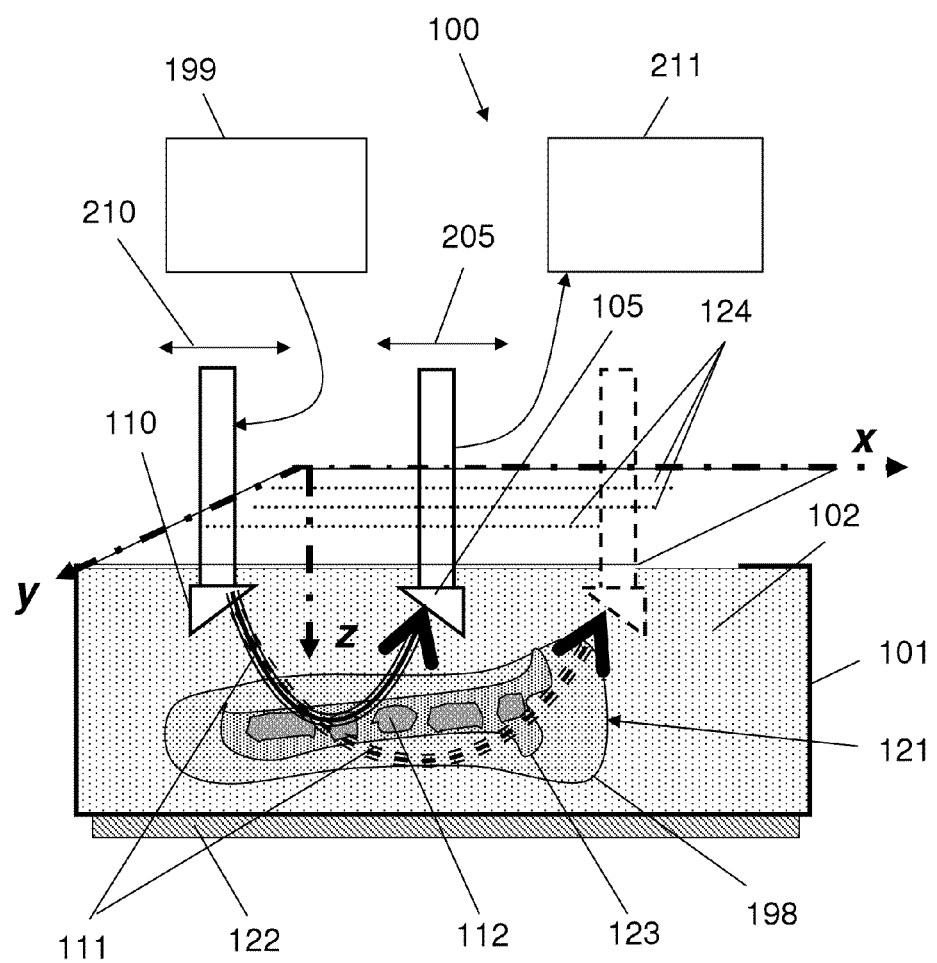
FIG. 11 illustrates the experimental arrangement that was used for the experimental demonstration and verification of the invention.

FIG. 11 schematically illustrates the experimental ultrasonic system that was used for the experiment to demonstrate and verify the validity of the invention.

Experimental system 100 uses only a single transmitter 110 and a single receiver 105. Both transmitter 110 and receiver 105 are immersed in a liquid 102 contained within a container 101. An object 121 to be observed is immersed in the liquid at the bottom of the container. Object 121 comprises leg bones 112 of a pig. The pig leg bone 112 is surrounded by soft tissue 123. A dry wooden plate 122 is positioned under container 101 in order to create the needed layer system. The filaments of wooden plate 122 are oriented parallel to that the bone so that the plate will not have a significantly larger acoustic impedance than the other layers. The pig leg sample was wrapped with an additional layer of chicken meat 198 to form a layered system.

In the experiment, the container 101 was 40 cm long in the X direction, 12 cm deep in the Y direction, and 17 cm wide in the Z direction. Imaging was carried out over 28.2 cm in its center.

Transmitter 110, oriented as depicted in the drawing, receives electronic signals from a pulse generator 199 and produces an ultrasonic beam 111. Beam 111 travels non-linearly within the complex layered volume comprised of liquid 102, soft tissue 198 of chicken meat, soft tissue 123 of the pig's leg, bones of the pig's leg 112, and plate 122 and after passing through at least some of these layers arrives at the receiver 105. A measuring unit 211 was used for extracting the time of travel information.

Mechanical translators (schematically depicted by the double headed arrows 210 and 205) were used for translating transmitter 110 and receiver 105 respectively to new locations along the x-axis. Depth penetration is measured along the z-axis. As is shown in the figure, the depth reached by ultrasonic beam 111 is dependent on the distance between transmitter 110 and receiver 105. For 3D imaging the imaging the transmitter and receiver were moved along the y-axis to a different virtual grid line 124.

The ultrasound generator used for this experiment was an old "concrete tester" made by C.S.I. (Holland). This device was not optimal for the purpose, yet it demonstrated the feasibility of the method according to the current invention.

Table 1, shown in FIG. 18, depicts experimental data obtained using the arrangement shown in FIG. 11. The experiments were carried out using only two transceivers that were moved along the x and y axes.

In Table 1 columns 3 to 10 are the measured transit times for the direct direction (columns 3, 5, 7, and 9) and for the reciprocal direction (columns 4, 6, 8, and 10). The transit time is measured in microseconds. Columns 3 and 4 list transit times between points (−m) and points (m), columns 5 and 6 list transit times between points (−m+1) and points (m−1), columns 7 and 8 list transit times between points (−m+1) and points (m), and columns 9 and 10 list transit times between points (−m) and points (m−1). Column 2 shows the distances between the transmitting and receiving transducers.

Column 1 of the table lists the points on the axis x (from "−m" to "m") relative to the considered column of the system being investigated. In this table there are three columns located at 9.2, 10 and 10.8 cm for which the measurements are represented. The incident angle for the ultrasonic beam was 45 degrees. The distance between transducers, which equals the step that they were moved was b=0.8 cm.

For example the column 10.8 cm is the axis for the elementary volumes situated in the column located between points 18-19. The minimal distances between transmitter and receiver the "−m" to "m" are points 12 ("−m") and 25 ("m"), which corresponds to the minimal depth of the beam penetration by the axis. The distance 5.2 listed in the second column of Table 1 is the distance between transmitter and receiver and also the depth of the beam penetration; in this case 5.2 cm=6.5 b.

For transmitter and receiver located at the points 11 ("−m") and 26 ("m") on the profile for the column located at 10.8 cm the distance between transmitter and receiver and also the depth of the beam penetration is 6 cm=7.5 b.

The treatment of the data was carried out according to the description above in relation to FIGS. 6A to 6D. The following parameters were used: $\Delta t_m = t_m + t_{m-1} t_{dir} - t_{rec}$. Where $t_m$ is the average value of the difference between the travel time of the longitudinal wave in the direct and reciprocal directions for one transducers arrangement (were m is a number representing the location of a transducer on the x-axis) from point m ("m" is the recurring greatness) to point (−m); $t_{m-1}$ is the average value of the difference between the travel time for the longitudinal wave in the direct and reciprocal directions for transducers arrangement from point (m−1) to point (−m+1); $t_{dir}$ is the average value of the difference between the travel time of the longitudinal wave in the direct and reciprocal directions for transducers arrangement from point (−m) to point (m−1) and $t_{rec}$ is the average value of the difference between the travel time for the longitudinal wave in the direct and reciprocal directions for transducers arrangement from point m to point (−m+1). In the experiment the sample was immersed in water. The velocity of an ultrasound wave in water is 1480 m/s (at 20.degree. C.).

Since the step of two-coordinate displacement of the transducers was 8 mm the length of the route that the wave traveled in a elementary volume of the first layer was $2 \times \sqrt{2} \times 8 = 22.63$ mm. The time of longitudinal wave travel in the first layer is thus computed to be $$t_1 = \frac{22.63 \times 10^{-3}}{1480} = 15.29 \ \mu s.$$

The length of longitudinal wave travels in each elementary volume in the layers below the elementary volume in the first layer, which is water is $S = 2\pi b = 25.12$ mm.

Table 2, shown in FIG. 19 shows parameters derived from Table 1 using the method described herein above for the specimen where soft tissues predominate.

Table 3, shown in FIG. 20, depicts the calculated longitudinal wave velocity values for another specimen where bone predominates. The calculations were carried out using the data in the Tables 1 and 2 (FIGS. 18 and 19). Table 3 shows the longitudinal wave velocity values corresponding to elementary volumes situated at the points with corresponding coordinates. The values of coordinates in the first vertical column of the table represent the distance along the y axis and in the third horizontal row corresponding to the distance along the x axis.

The measured results for the longitudinal wave velocity in each of the elementary volumes are used to construct images that represent images of the longitudinal wave velocity in the object that was measured. One of the major advantages of the present invention is that these images can be analyzed to identify the objects in the image and carrying out diagnoses by utilizing distinctive values of the longitudinal wave velocity for the features in the images. This is possible because each healthy organ has its own values of longitudinal wave velocity and estimated physical-mechanical properties. For example, the approximate longitudinal wave velocity values in different human bodily tissues and organs are: soft tissue—about 1540 M/S; bone—about 1700-5000 M/S; fatty tissue—about 1450 M/S; liver—about.—1550 M/S; blood—about 1570 M/S; muscle about 1580 M/S. Changes in the velocities may indicate diseased or injured tissue such as fractured or osteoporotic bone. The approach of the invention is especially useful in the case of bone inspections because of the wide range of elastic wave velocity changes that exists for bone media.

Figure 12:
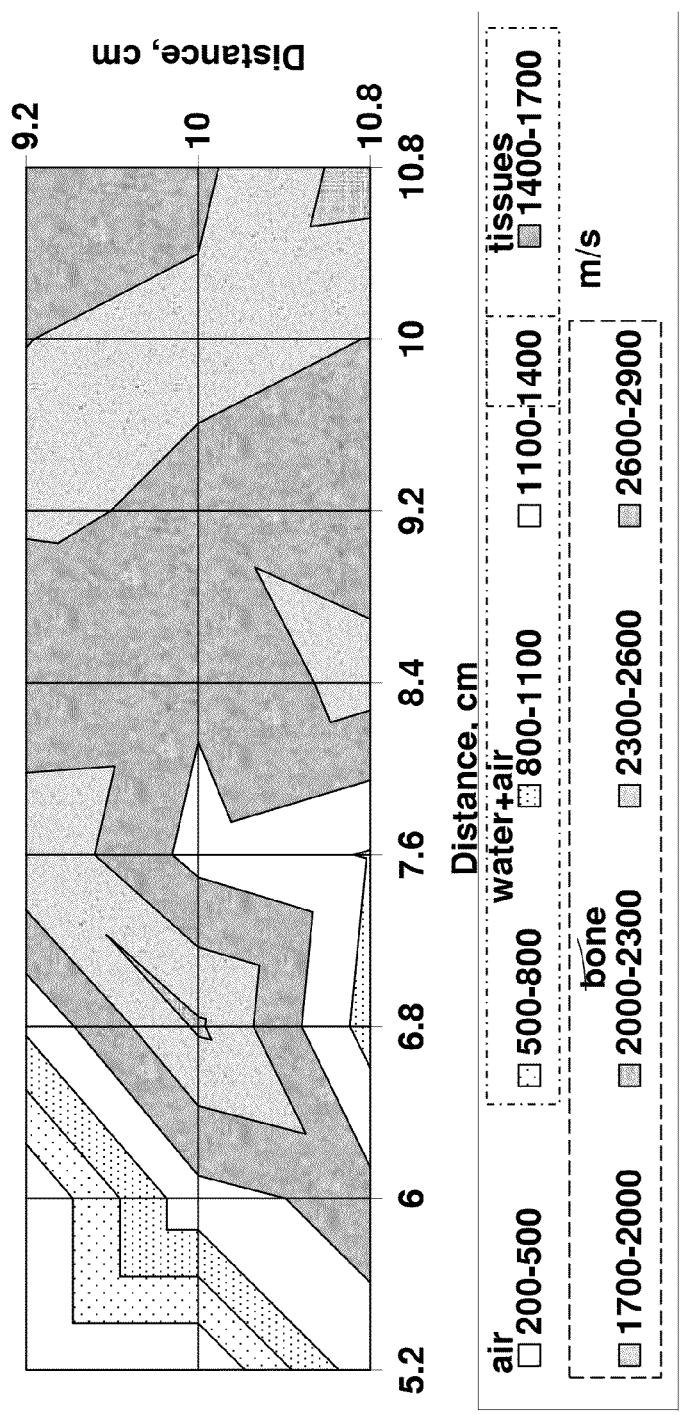
FIG. 12 is a map showing experimental results for the distribution of longitudinal wave velocity values in a specimen.

FIG. 12 is a 2D image showing the distribution of the longitudinal wave velocity values in the object. The figure shows the type of details that can be learned from the obtained images and demonstrate the possibility of revealing anatomical details for diagnostics purposes. The image in FIG. 12 was obtained as a result of the inspection of a specimen, which included both soft tissue (meat) and bone media, and in which bone media predominates. The longitudinal velocity values measured are within ranges that relate to different components of the layered system as follows: air—360 up to 500 m/s; water containing air—500 to 1480 m/s; soft tissues 1400-1600 m/sec; and for bone tissues from 1700 to 2900 m/s. Thus the locations of bone, soft tissues and water in the image can easily be identified by the distribution of velocities that is determined by using the method of the invention. The 2D image of longitudinal wave velocity distributions in the object shown in FIG. 12 was obtained from the obtained data in Table 2 using Microsoft "Excel" programming.

Another major use of the invention is to provide an estimation of the porosity of the inspected object. Wave velocity in each elementary volume of a bone matrix can be used to distinguish between the mineral part of bone tissue and the pores filled with bone marrow.

Figure 13:
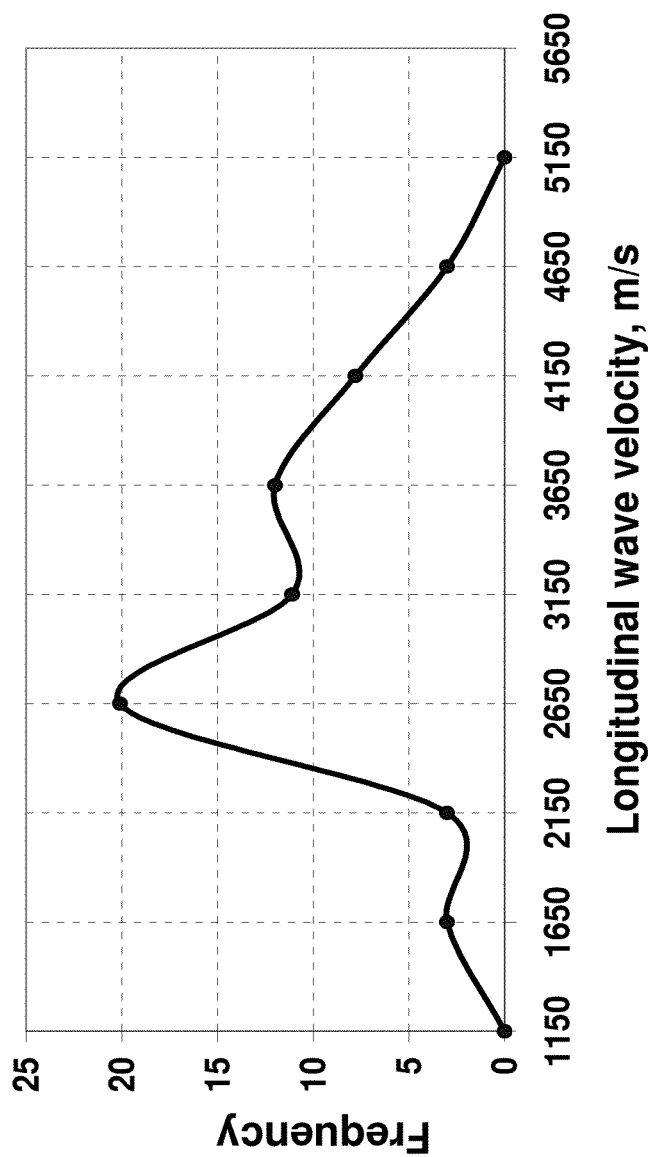
FIG. 13 is a graph of experimental results showing the frequency of occurrence, i.e. number of elementary volumes, vs. longitudinal wave velocity.

The estimation of the porosity is provided by applying statistical treatment of the data obtained for a plurality of elementary volumes of an inspected object. The value of the longitudinal wave velocity $V_t$ in the mineral part of the bone under consideration may be considered as the maximum value of a graph showing the distribution of longitudinal wave velocity values. The graph shows frequency of occurrence, i.e. number of elementary volumes, vs. longitudinal wave velocity that summarizes the statistical treatment of data for a specimen of meat with bone in which bone tissue predominates is shown in the FIG. 13. According to the graph the value $V_t$=5150 m/s may be taken as the longitudinal wave velocity in the matrix (skeleton) of the bone.

The value n of porosity expressed by the changed Wyllie relationship cited in the background section herein above can be defined from the "Equation of average time". This equation is:

$$\frac{1}{V_p} = \frac{1-n}{V_t} + \frac{n}{V_{fill}}$$

According to the invention, the porosities values n can be calculated using the values of the corresponding elastic waves travel times in the elementary volumes of an inspected object, where $V_t$ is the longitudinal wave velocity in the bone, $V_p$ is the velocity in the matrix part of the bone, and $V_{fill}$ in the filling of the medium water.

The previous equation is solved for the porosity n to yield:

$$n = \frac{(V_t - V_p)V_{fill}}{V_p(V_t - V_{fill})}$$

The porous medium in a bone substance is filled by marrow. The approximate value of the velocity in the filling may be taken as equal to 1550 m/s in the case of human bones. Using data from Table 3 (FIG. 20), the porosity was calculated for a plurality of elementary volumes of a specimen, comprising meat and a predominantly bone part. The obtained porosity values are depicted in FIG. 21, which shows Table 4.

While presently used methods of studying bones in vivo measure only one parameter, i.e. Bone Mineral Density (BMD), the present invention provides the possibility for carrying out bone inspections and estimating the values of a number of parameters associated with the bone material as well as with its structural properties and provides the possibility for 3D imaging showing quantitative estimations of these parameters for an inspected volume. The method of the invention provides an estimate of bone strength from two different points of view. On the one hand estimates of the velocity in the mineral part of the bone are direct indications of the strength of the bone and on the other hand measurements and imaging of the porosity give an indication of weakness in the bone and locations of potential cracks or fractures. The parameters of bone media that can be estimated using the method of the invention include, for example: bone porosity, longitudinal wave velocity, longitudinal wave velocity and porosity distribution in an inspected volume, longitudinal wave velocity in the bone's skeleton (the bone matrix part) a, evaluation of the risk of fracture and its location is possible by analysis of the obtained images.

Figure 14:
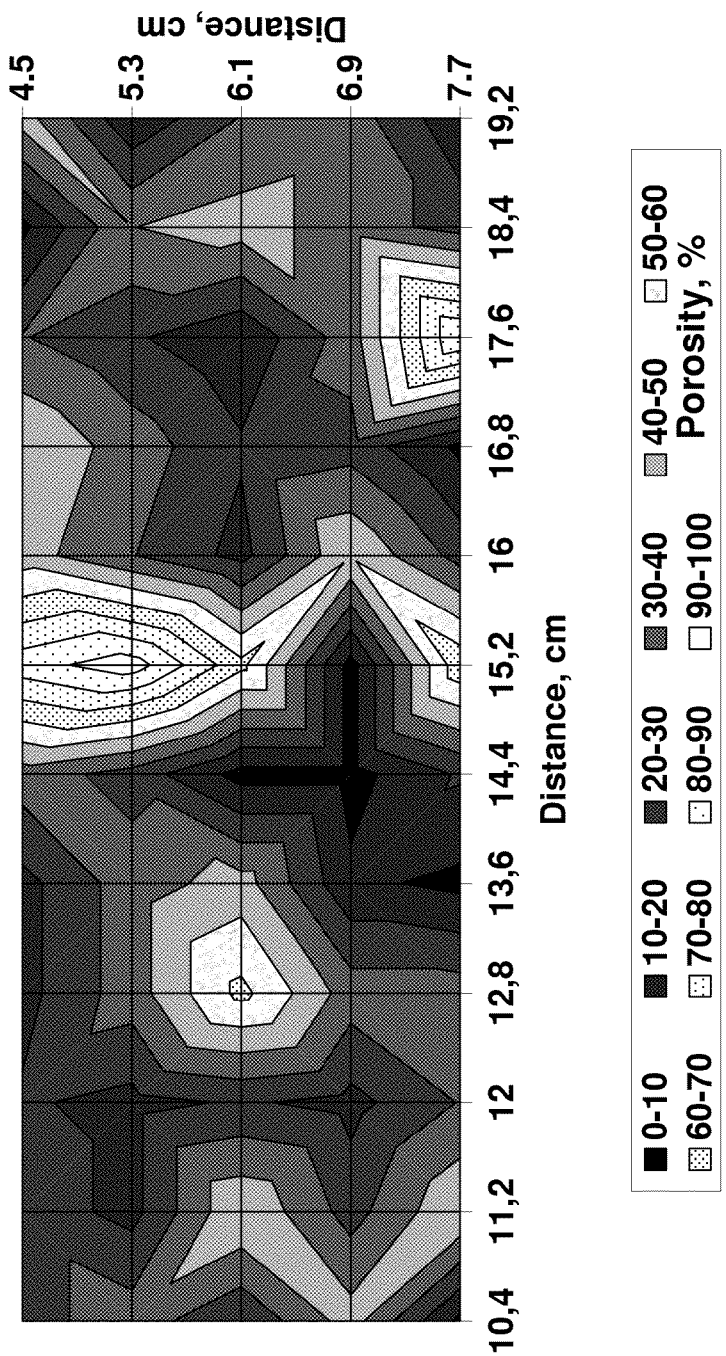
FIG. 14 shows experimental results for the distribution of porosity values in a section of pig's leg.

FIG. 14 shows the distribution of porosity values in a specimen comprising meat and bone in which the main component is bone media.

Experiments were performed using different types of beef with bones. The results of some of these experiments are presented in FIG. 7A and FIG. 7B. The results of the experiments are presented as images showing determined longitudinal wave velocities values and distributions of porosity values. The experiments confirm the viability of the method of the current invention and its applications to the human bodies as well as for non-medical uses.

Figure 15A:
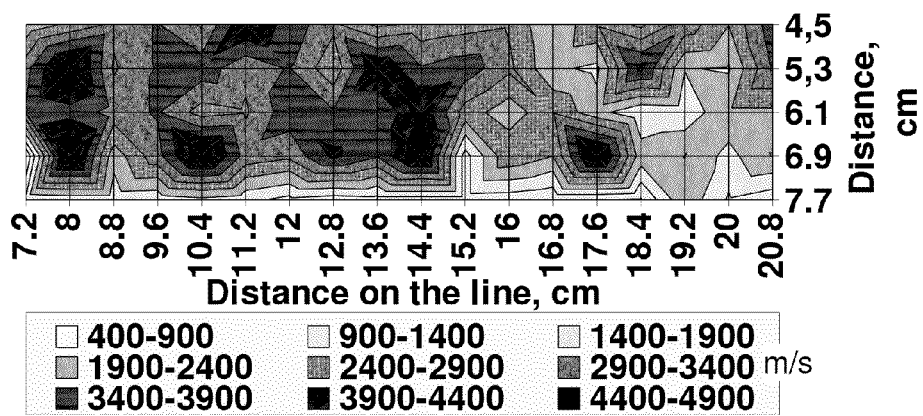
FIG. 15A and FIG. 15B illustrate experimental results demonstrating the use of the method of the invention for diagnosing bone damage by comparison of images obtained for a pig's leg before and after mechanical damages were intentionally inflicted.
Figure 15B:
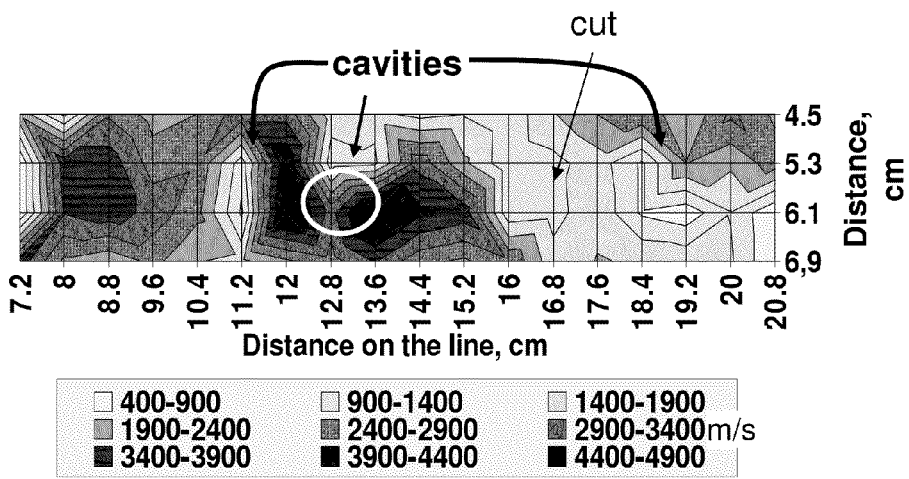

In order to demonstrate the use of the method of the invention for diagnosing injury and locating physical damage to a bone the pig's leg specimen was evaluated before and after impacting it with few heavy blows and inflicting a deep cut in the middle part of the specimen. The images obtained by the method of the invention "before" and "after" the blows and cut were inflicted are shown in FIG. 15A and FIG. 15B respectively. FIGS. 15A and 15B depict the maps of longitudinal wave velocity values distributions in the section of the pig's leg that was inspected. Cavities and a crack caused by the inflicted blows are revealed by reduction in the values of the velocities in the comparable elementary volumes in the two images seen. These images illustrate the possibility of revealing the damaged zone in the obtained image. For example, the presence of a crack resulting from one of the impacts in the elementary volume at 12.8 cm can be seen by the decrease of the value of longitudinal wave velocity in this zone from 3400-3900 m/s to 2400-2900 m/s.

Figure 16:
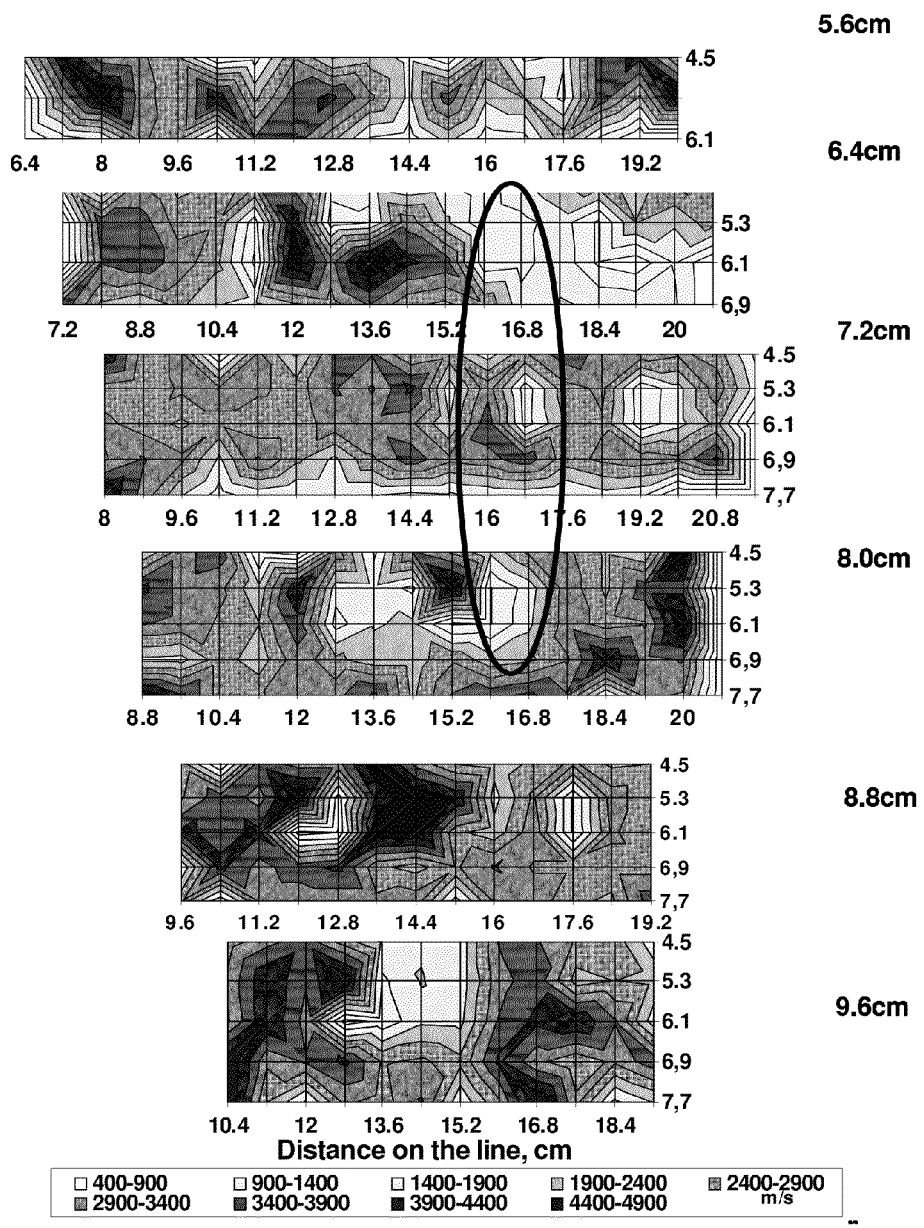
FIG. 16 shows experimental results and illustrates how a series of 2D sections shifted along a third axis with a step b=8 mm can be integrated to form a quantitative 3d image.

FIG. 16 illustrates how a series of 2D sections shifted along a third axis with a step b=8 mm can be integrated to form a quantitative 3D image. The horizontal axes in the slices shown in FIG. 16 correspond to the x-axis in the experimental set up shown in FIG. 11; the vertical axes in FIG. 16 correspond to the z-axis in FIG. 11; and the slices are taken along the y-axis in FIG. 11. The 2D images show the distributions of the longitudinal wave velocity for the pig's leg specimen that was damaged to produce the image shown in FIG. 15B. In this case the leg was wrapped with meat (muscle mass) for creation of the layered system and immersed in a container containing water. The ellipse shows the changes in velocity from section to section caused by the cut in the bone.

The regions with the cut can be detected by the lower longitudinal wave velocity values in the sections 6.4, 7.2, 8 cm. Section 5.6 cm is through the muscle mass that was wrapped around the leg but does not cut through the bone that was cut; therefore the velocity in this slice at the location of the cut in the previous slices is higher. Each of the 2D images is built up from a large number of independent measurements and the fact that the image of the damaged place in the object is repeated from image to image proves the proposed technology.

Figure 17:
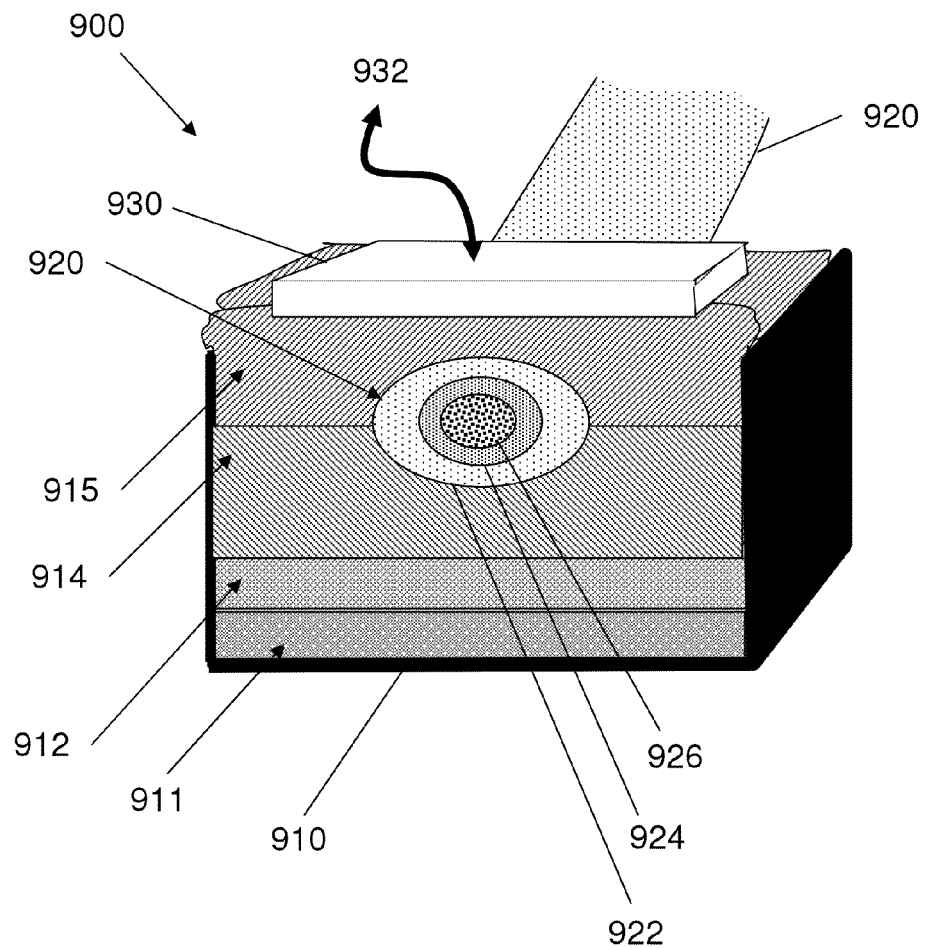
FIG. 17 schematically depicts an apparatus providing an artificial layered system characterized by an acoustic impedance gradient for inspection of an object by the method of the invention.

FIG. 17 schematically depicts an apparatus for using the method of the current invention for in vivo inspection of a part of a human body such as a local heterogeneous region comprised of skin 922, the soft tissue between the skin 922 and the bone 924, and the bone marrow 926.

The three dimensional ultrasonic system 900 to be used for evaluation of local heterogeneous region 920 comprises an assembly consisting of different layers to provide the needed condition for propagation of non-linear beams in a volume being inspected.

An optional "U" shaped solid frame 910 is supplied to support one or more layers 911, 912, 914 of different materials to provide an acoustic impedance gradient and to support the local heterogeneous region to be inspected. The number and composition of the layers are selected according to the part of the patient to be scanned and also according to the characteristics of the patient, e.g. thin or overweight, etc. In some situations the frame 910 is not used and the bottom layers are placed on an examination table. A top pillow 915 having the correct acoustic impedance is used for covering the local heterogeneous region and a 2D transducer array 930 is placed on top of the top pillow which interfaces between the curved limb and the flat array. Array 930 receives signals from, and transmits signals to controller 932 which comprises the elements depicted in FIG. 11.

If examination of structures in the lower part (away from transducer 930) is not important, then the bottom layers are not needed. For example, the spinal structures of a patient may be examined by placing the patient in a prone position on his stomach with only a top pillow on his back.

It is to be appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub combination.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

The invention claimed is:

1. A differential method of 3D Quantitative-Imaging Ultrasonic Tomography for inspecting a layered system comprised of a heterogeneous object embedded in a volume of space that comprises layers having an acoustic impedance gradient between said layers, wherein said acoustic impedance gradient causes non-linear elastic wave propagation of ultrasonic oscillations through said volume of space, said method comprising:
   a) providing two or more transducers arranged in a line or as a two-dimensional array on one side of the layered system and in acoustic contact with the upper layer of said layered system, said transducers capable of being activated to either transmit or to receive said ultrasonic oscillations;
   b) sequentially activating one of said transducers as a transmitter and others of said transducers as receivers of said ultrasonic oscillations to measure the fastest travel times for sequential transmitter/receiver pairs with sequentially changing distances between transmitter and receiver;
   c) virtually dividing said volume of space into elementary volumes;
   d) using a differential approach to determine values of the longitudinal wave velocity for each of said elementary volume; and
   e) applying an ultrasonic computer tomography approach to construct two-dimensional and three-dimensional maps of the distributions of said longitudinal wave velocity values in said volume of space.

2. The method of claim 1 further comprising the steps of:
   f) determining a correct magnitude of frequency of the ultrasonic oscillations to be used with the transducers and the arrangement of the transducers for inspection in a specific application;
   g) activating a first transducer to transmit ultrasonic oscillations in the direction of an object being observed and activating the remaining transducers to receive elastic waves that have traveled through the observed layered system;
   h) measuring the fastest time of travel between each transmitter-receiver pair and storing said travel times for later use;
   i) repeating the measurements sequentially by changing the distance between transmitter and receivers by a fixed distance equal to distance between transducers each time;
   j) repeating measurements of steps g), h), and i) in the reciprocal direction;
   k) moving the line of transducers parallel to the original line or activating a second line of transducers in a two dimensional grid of transducers and repeating the measurements of steps g), h), i), and j) in the direct and reciprocal directions until data is obtained from each line in the transducer grid;
   l) dividing virtually the volume of space containing the layered system into elementary volumes situated in columns and rows, thereby enabling use of a differential approach to processing the data obtained from each line in the transducer grid;
   m) determining from the obtained data the values of changes in longitudinal wave travel time in each of said elementary volumes relative to the elementary volume located above it in the column from average values of the longitudinal wave travel times for neighboring routes in direct and reciprocal directions said determination comprising the steps of:
      i) choosing two pairs of transducers located at two neighboring points equidistant from an axis of a column of elementary volumes;
      ii) summing the values of the travel time for ultrasonic oscillations between the transducers of each of said pairs that are furthest from said axis and the travel time for ultrasonic oscillations between the transducers of each of said pairs that are closest to said axis;
      iii) subtracting from the sum obtained in step ii the travel times for ultrasonic oscillations between the transducer of the pair of transducers located on a first side of said axis that is closest to said axis and the transducer of said pair of transducers that is located on the second side of said axis that is furthest from said axis;
      iv) subtracting from the sum obtained in step iii the travel times for ultrasonic oscillations between the transducer of the pair of transducers located on a first side of said axis that is furthest from said axis and the transducer of said pair of transducers that is located on the second side of said axis that is closest to said axis;
      v) repeating steps i to iv using different pairs of transducers for each of the elementary volumes in said column; and
      vi) repeating steps i to v for each column of elementary volumes in said volume of space containing the layered system;
   n) determining the values of longitudinal wave travel times for each elementary volume in each vertical column of elementary volumes by using the known or previously measured value of the longitudinal wave travel time in the first elementary volume from the surface and by successively adding said values of the changes of the longitudinal wave travel times for the elementary volumes below said first one in said column;
   o) estimating the lengths of travel of the longitudinal wave through each of said elementary volumes;

p) determining the longitudinal wave velocity values in each of said elementary volumes by dividing said estimated lengths of travel of the longitudinal wave through each of said elementary volumes by said values of longitudinal wave travel times for each elementary volume in each vertical column of elementary volumes;

q) building pixel-by-pixel images of two dimensional horizontal or vertical sections from the longitudinal wave velocity values in each of said elementary volumes; and r) combining said two dimensional images along a third axis with a constant step to build three dimensional images showing said longitudinal wave velocity values in said volume of space.

3. The method of claim 2, wherein at least some of the steps are carried out in a different order.

4. The method of claim 2, wherein determining the correct magnitude of the frequency of the ultrasonic oscillations to be used with the transducers and the arrangement of the transducers for the inspection in a specific application are determined using the following criteria:

a) the frequency is chosen such that the length of the applied oscillations are comparable to the dimensions of the inspected heterogeneous object; and b) the distance between the first transmitting transducer and the last receiving transducer in the line must be greater than the dimensions of said inspected heterogeneous object.

5. The method of claim 2, wherein the ultrasonic oscillations are transmitted in the direction of an object being observed at an angle of no more than ninety degrees.

6. The method of claim 2, wherein the minimum distance between a transmitting transducer and a receiving transducer is two to three wavelengths of the applied oscillations.

7. The method of claim 2, wherein the length of travel of the longitudinal wave in each elementary volume is approximated by assuming that the longitudinal waves travel the same distance in each of the elementary volumes beneath the elementary volumes of the first layer of layered system; wherein said distance is half the circumference of a circle having radius b, where b is the distance between adjoining transducers; and by assuming that the wave travels in straight lines through the elementary volumes of the first layer, therefore the length of travel time in the first layer is $2b/\sin\alpha$ where $\alpha$ is the incident angle of the oscillations on the first layer.

8. The method of claim 2 wherein the acoustic properties of the uppermost elementary volumes are known or can be calculated.

9. The method of claim 2 wherein the acoustic properties of the uppermost elementary volumes are known in one of the following ways:

a) by implementing the first layer of the system as an additional plate or pillow having known acoustic properties; and b) immersing the system in a container with liquid having known acoustic properties.

10. The method of claim 9, wherein analyzing the obtained maps by observing decreases in the values of the elastic wave velocities and increases in porosity values that are shown in different areas of said images reveals defective areas in the inspected object.

11. The method of claim 10, wherein the layered system is a human or animal body including bone material and analysis of the obtained images reveals defective areas that are problematical zones with fracture risk, estimates of the magnitude of the risk of fracture and reveal the location of the risk by calculating the ratio of relative changes of the longitudinal wave velocity values for said defective area divided by the longitudinal wave velocity in the material matrix of the object.

12. The method of claim 9, wherein analysis of the obtained maps is carried out to provide information about internal organs of an individual and to reveal changes in the properties of said organs.

13. The method of claim 2, wherein a combination of signals from eight beams transmitted in the direct and reciprocal directions is employed to determine the properties of a specific elementary volume in the observed object.

14. The method of claim 2, wherein a combination of signals from four beams transmitted in the direct direction or four beams transmitted in the reciprocal direction is employed to determine the properties of a specific elementary volume in the observed object.

15. The method of claim 2, further comprising the steps of:

i) applying statistical treatment to the longitudinal wave velocity values obtained in step p) to determine the maximum value of the longitudinal wave velocity;

ii) identifying a matrix mineral part of an observed object, wherein said matrix mineral part of the object corresponds to elementary volumes that have said maximum value of longitudinal wave velocity;

iii) determining the values of porosity for each elementary volume of an observed volume by use of the modified Wyllie relationship for objects wherein the porous space is filled with liquid;

iv) building pixel-by-pixel images of two dimensional horizontal or vertical sections from said values of porosity for each elementary volume; and v) combining said two dimensional images along a third axis with a constant step to build three dimensional images showing the porosity values in said observed volume.

16. The method of claim 2, wherein the layered system is at least a part of a human or animal body wherein the layers comprise skin, fat, periosteum, cartilage, and muscle and bones are considered as localized heterogeneous bodies embedded in said layered system.

17. The method of claim 2, wherein the elementary volumes are cubes having sides equal in length to the distance between two adjacent lines on the 2D planar grid or distance between transducers.

18. The method of claim 1, wherein at least one of the layers of the layered system is an artificial layer that is applied to create a layered system having a gradient of acoustic impedance that allows said differential method to be carried out.

19. The method of claim 1, wherein inspecting a layered system comprises inspecting homogeneous material accommodated in said layered system, which is characterized by an acoustic impedance gradient.

* * * * *